US008288128B2

(12) United States Patent
Remacle et al.

(10) Patent No.: US 8,288,128 B2
(45) Date of Patent: Oct. 16, 2012

(54) REAL-TIME QUANTIFICATION OF MULTIPLE TARGETS ON A MICRO-ARRAY

(75) Inventors: José Remacle, Malonne (BE); Isabelle Alexandre, Namur (BE); Sylvain Margaine, Namur (BE); Dieter Husar, Namur (BE)

(73) Assignee: Eppendorf Array Technologies S.A., Namur (BE)

( * ) Notice: Subject to any disclaimer, the term of this patent is extended or adjusted under 35 U.S.C. 154(b) by 1665 days.

(21) Appl. No.: 10/991,087

(22) Filed: Nov. 18, 2004

(65) Prior Publication Data

US 2006/0105354 A1    May 18, 2006

(51) Int. Cl.
C12P 19/34 (2006.01)
C12Q 1/68 (2006.01)

(52) U.S. Cl. ........................................ 435/91.2; 435/6.1
(58) Field of Classification Search .................. 435/6
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 5,744,305 A | 4/1998 | Fodor et al. | |
| 6,346,413 B1 | 2/2002 | Fodor et al. | |
| 6,416,951 B1 | 7/2002 | Schmidt et al. | |
| 6,589,740 B2 | 7/2003 | Nakao et al. | |
| 2002/0177135 A1* | 11/2002 | Doung et al. | 435/6 |
| 2003/0128910 A1* | 7/2003 | Naghieh et al. | 385/15 |

FOREIGN PATENT DOCUMENTS

| | | |
|---|---|---|
| WO | WO 97/10365 A1 | 3/1997 |
| WO | WO 97/27317 A1 | 7/1997 |
| WO | WO 99/20789 A1 | 4/1999 |
| WO | WO 99/32660 A1 | 7/1999 |
| WO | WO 01/77372 A2 | 10/2001 |
| WO | WO 02/18288 A1 | 3/2002 |
| WO | WO 03/052421 A1 | 6/2003 |

OTHER PUBLICATIONS

Arena et al. IEE Engineering in Medicine and Biology, Mar./Apr. 2002, pp. 17-25.*
Bier et al., "Feature-size limitaions of microarray technology—a critical review," *Fresenius J. Anal. Chem.*, Sep. 2001, pp. 151-156, vol. 371, No. 2, Springer-Verlag.
Bier et al., "Real-time analysis on microarray," *Anal. Bioanal. Chem.*, 2004, pp. 52-53, vol. 378, Springer-Verlag.
Boyer et al., "Photothermal Imaging of Nanometer-Sized Metal Particles Among Scatterers," *Science*, Aug. 16, 2002, pp. 1160-1163, vol. 297.

Caruso et al., "Quartz Crystal Microbalance Study of DNA Immobilization and Hybridization for Nucleic Acid Sensor Development," *Anal. Chem.*, Jun. 1, 1997, pp. 2043-2049, vol. 69, No. 1, American Chemical Society.
Cognet et al., "Single metallic nanoparticle imaging for protein detection in cells," *PNAS*, Sep. 30, 2003, pp. 11350-11355, vol. 100, No. 20, The National Academy of Sciences of the USA.
Han et al., "Quantum-dot-tagged microbeads for multiplexed optical coding of biomolecules," *Nature Biotechnology*, Jul. 2001, pp. 631-635, vol. 19, Nature Publishing Group.
Lehr et al., "Real-Time Detection of Nucleic Acid Interactions by Total Internal Reflection Fluorescence," *Anal. Chem.*, May 15, 2003, pp. 2414-2420, vol. 75, No. 10, American Chemical Society.
McKendry et al., "Multiple label-free biodetection and quantitative DNA-binding assays on a nanomechanical cantilever array," *PNAS*, Jul. 23, 2002, pp. 9783-9788, vol. 99, No. 15.
Moreno-Hagelsieb et al., "Sensitive DNA electrical detection based on interdigitated $Al/Al_2O_3$ microelectrodes," *Sensors and Actuators B*, 2004, pp. 269-274, vol. 98.
Ozsoz et al., "Electrochemical Genosensor Based on Colloidal Gold Nanoparticles for the Detection of Factor V Leiden Mutation Using Disposable Pencil Graphite Electrodes," *Anal. Chem.*, May 1, 2003, pp. 2181-2187, vol. 75, No. 9, American Chemical Society.
Thiel et al., "In Situ Surface Plamon Resonance Imaging Detection of DNA Hybridization to Oligonucleotide Arrays on Gold Surfaces," *Anal. Chem.*, Dec. 15, 1997, pp. 4948-4956, vol. 69, No. 24, American Chemical Society.
Wei et al., "Monitoring DNA hybridization on alkyl modified silicon suface through capacitance measurement," *Biosensors and Bioelectronics*, 2003, pp. 1157-1163, vol. 18, Elsevier Science B.V.
McQuain et al., "Chaotic mixer improves microarray hybridization," *Analytical Biochemistry*, Feb. 15, 2004, pp. 215-226, vol. 325, No. 2, Academic Press, San Diego, CA USA.

(Continued)

*Primary Examiner* — Gary Benzion
*Assistant Examiner* — Cynthia Wilder
(74) *Attorney, Agent, or Firm* — Foley & Lardner LLP

(57) ABSTRACT

The present invention relates to a method and apparatus for monitoring a real-time quantification of multiple target molecules during their binding on capture molecules of a micro-array. The method comprises the steps of: placing, in a chamber (14), a support (15) having fixed upon its surface a micro-array comprising at least 5 capture molecules (20) being immobilized in specifically localized areas (21) of said support; introducing said labeled target molecules solution (13) into the chamber; incubating said labeled target molecules under stable and controlled temperature conditions to allow the binding between said target and capture molecules; directing an excitation light (2) from a light source (1) on the surface of the micro-array; measuring the electromagnetic light emission (7) from the bound target molecules in response to said excitation light in presence of the solution containing the target molecules wherein the surface of emission for a localized area is comprised between about 0.1 $\mu m^2$ and about 10 $mm^2$ and wherein each of the at least 4 localized areas is monitored with time with at least two measurements being done per localized area (21), and processing and storing the values of the different measurements and quantifying at least 4 different target molecules present in solution using at least one measurement value for each said target.

29 Claims, 12 Drawing Sheets

OTHER PUBLICATIONS

Lehr et al., "Modeling and experimental verification of the performance of TIRF-sensing systems for oligonucleotide microarrays based on bulk and integrated optical planar waveguides," *Sensors and Actuators B*, Jul. 15, 2003, pp. 303-314, vol. 92, No. 3, Elsevier Sequoia S.A., Lausanne, CH.

Zammatteo et al., "Comparison between microwell and bead supports for the detection of human cytomegalovirus amplicons by sandwich hybridization," *Analytical Biochemistry*, 1997, pp. 180-189, vol. 253, No. 2, Academic Press, San Diego, CA USA.

Bier et al., "Real-time analysis on microarrays," *Analytical and Bioanalytical Chemistry*, Jan. 2004, pp. 52-53, vol. 378, No. 1.

Schwonbeck et al., "Cohort anaylisis of a single nucleotide polymorphism on DNA chips," *Biosensors & Bioelectronics*, Nov. 15, 2004, pp. 956-966, vol. 20, No. 5, Elsevier Science Publishers, Banking, GB.

Lehr et al., "Real-time detection of nucleic acid interactions by total internal reflection fluorescence," *Analytical Chemistry*, May 15, 2003, pp. 2414-2420, vol. 75, No. 10, American Chemical Society, Columbus, OH USA.

Nice et al., "Instrumental biosensors: new perspectives for the analysis of biomolecular interactions," *Bioessays*, Apr. 1999, pp. 339-352, vol. 21, No. 4, Cambridge, GB.

Hutchinson, "Evanescent wave biosensors. Real-time analysis of biomolecular interactions," *Molecular Biotechnology*, Feb. 1995, pp. 47-54, vol. 3, No. 1.

Wei et al., "Monitoring DNA hybridization on alkyl modified silicon surface through capacitance measurement," *Biosensors and Bioelectronics*, Aug. 15, 2003, pp. 1157-1163, vol. 18, No. 9.

\* cited by examiner

REAL-TIME QUANTIFICATION OF MULTIPLE TARGETS ON A MICRO-ARRAY

FIELD OF THE INVENTION

The present invention relates to a method and an apparatus for monitoring in real-time the quantitative binding of multiple target molecules to capture molecules of a micro-array. More particularly, the invention comprises detecting in real-time the hybridization between capture DNA molecules spotted on a micro-array and sample nucleotides, such as fluorescence-labeled DNA present in solution.

DESCRIPTION OF THE RELATED ART

To obtain the maximum information about the smallest amount of sample is one of the major objectives of analytical science. This holds particularly true in molecular biology and in all molecular based life science where there is a demand for a highly parallel analysis. Micro-array technology is one answer to this demand. It enables massive parallel determinations and multiple measurements for binding events to be performed simultaneously in the same solution. Micro-arrays usually consist of many microscopic spots each one containing identical molecules, i.e. nucleic acids or proteins acting as capture molecules. The number of spots can vary from less than one hundred to several thousand. The molecules are immobilized to a solid support by an attachment preferably by covalent link. The primary task of a micro-array experiment is to simultaneously detect many binding events.

Since it provides high sensitivity, fluorescence is used in most applications as a label to detect the binding events. Prior to carrying out the experiment, the sample must be labeled by means of a suitable fluorochrome. Binding is achieved in a separate incubation step and the final result is obtained after appropriately washing and drying the micro-array. Micro-array readers usually acquire information about the fluorescence intensity at a given time of the binding process that would ideally be the time after arriving at the thermodynamic equilibrium. However, under the conventional conditions employed in the chip experiments, the thermodynamic equilibrium is difficult to obtain and not reached at the same time for the different targets, being present in a biological sample at different concentrations that may vary by several logs scale, because of several limitations such as the difference in the kinetic, the diffusion constant and the concentration of capture molecules.

In a fixed experiment setting, It is almost impossible to settle down experimental conditions in which the amount of target bound to its capture molecule would be directly proportional to the solution concentration.

The quantification step which follows the binding step on the micro-array is made after several steps of washing and implies that some essential information regarding the target sample are definitely lost such as the kinetics of the binding reaction.

One solution to the problem of concentration dependence binding of different targets present in a single sample would be the observation of the binding reaction in real-time for each individual target present in the solution.

Bier et al. (2004, Anal. Bioanal. Chem., 378, 52-53) teach the necessity to bring together a fluid-handling approach combined with an integrated detection scheme to render possible real-time analysis on micro-arrays. Enzyme reactions are exemplified in real-time on spots carrying labeled double stranded DNA. The immobilized DNA serves both, as a binding receptor for the enzyme and as substrate to be cleaved by the enzyme activity. After addition of the cofactor $Mg^{2+}$, the spots in which the DNA is cleaved by the enzyme are identified by the decrease in the fluorescence intensity (negative assay).

Bier and Kleinjung (2001, Fresenium J. Anal. Chem., 371, 151-156) propose to measure the hybridization kinetics mainly in the dissociation phase by obtaining melting curves for each spot of the micro-array. Following the same idea, U.S. Pat. No. 6,589,740 discloses means to detect hybridization reaction of fluorescent targets upon chips. Images of the reaction are taken at predetermined timings while running a washing solution into the container and while changing the temperature of the biochip. Melting curves are obtained by washing the chip at increasing temperatures. As the temperature is raised, sample DNA with weaker binding ability begin to dissociate from the probe DNA and the dissociated sample DNA is removed from the spots with the washing solution. Accordingly, the amount of hybridized fluorescence-labeled sample DNA decreases with lapse of time, and so as the fluorescent intensity.

The U.S. Pat. No. 6,416,951 teaches another method for measuring in real-time the kinetics of hybridization of RNA with a polynucleotide probe. The kinetics are measured by either hybridizing in the presence of an intercalation dye and recording a change in the spectroscopic properties of the dye as hybridizing proceeds, or incorporating a label in either the RNA or the probe, attaching the non-labeled molecule to a solid support, generating an evanescent wave in the proximity of the non-labeled molecule and recording the increase in a signal generated by interaction of the evanescent wave with the label, as hybridization proceeds.

WO9920789 discloses a method also based on the generation of evanescent wave used to scatter light from a particulate label adsorbed at multiple DNA capture zones placed on a wave guide surface. Since an evanescent wave only extends a few hundred nanometers from the wave-guide surface, the unbound/dissociated label does not scatter light and a wash step is not required. The desorption of the light-scattering label can be studied in real-time.

Real-time detection of nucleic acid interactions may also be obtained by total internal reflection fluorescence (Lehr et al. 2003, Anal. Chem. 75, 2414-20). The principle of total internal reflection fluorescence is based on alternating pattern of dark and bright areas and uniform evanescent illumination of the active sensor area.

WO03/052421 describes an electro-chemical analysis device for monitoring nucleic acids detection. The device comprises a biosensor, which is formed of a gold electrode having a plurality of probes attached thereto and an integrated thermal sensor. Analysis of molecular interaction is achieved at the biosensor site based on electrical detection.

Wie et al. (2003, Biosensors and Bioelectronics, 18, 1157-1163) propose to monitor DNA hybridization on alkyl modified silicon surface through real-time capacitance measurement.

A problem underlying the present invention resides in providing an improved method for quantifying the binding of target probes to capture molecules in real-time, obviating the shortcomings associated with prior art methods. Specifically, the method should be simple to carry out and cost effective.

The present invention aims to overcome most of these limitations by proposing a simple and effective method and apparatus for the simultaneous quantification of multiple target molecules on a micro-array. The invention proposes a method and apparatus for continuous monitoring of a target binding process in presence of the labeled targets present in solution with quantitative measurements being some of the critical improvements described in the present invention. The method is also useful for more complex experimental setting such as online with PCR amplification or can be adapted for functional studies such as protein affinity determination.

SUMMARY

The method allows to detect femtomoles or less of targets molecules bound to their capture molecules in real-time in the presence of the labeled molecules being present in the solution.

In order to realize the above-mentioned objectives, the method of the invention for the real-time quantification of multiple target molecules being labeled and present in a solution (13) on a micro-array comprises the following steps:

placing, in a reaction chamber (14), a support (15) having fixed upon its surface a micro-array comprising at least 5 capture molecules (20) being immobilized in specifically localized areas (21) of said support, introducing said labeled target molecules solution (13) into the reaction chamber (14), incubating said labeled target molecules under stable and controlled temperature conditions to allow specific binding between said targets and their corresponding capture molecules, directing an excitation light (2) from a light source (1) on the surface of the support, measuring the electromagnetic light emission (7) from the bound target molecules in response to said excitation light (2) in the presence of solution containing the target molecules wherein the surface of emission for a localized area is comprised between about 0.1 $\mu m^2$ and about 10 $mm^2$ and wherein each of the at least 4 localized areas (21) is monitored with time with at least two measurements being done per localized area, and processing and storing the values of the different measurements and quantifying at least 4 different target molecules present in solution using at least one measurement value for each said target.

The apparatus for real-time quantification on micro-array of multiple target molecules (13) according to the present invention comprises two parts, the first part being composed of:

a support (15) having fixed upon its surface a micro-array, comprising at least 5 capture molecules (20) being immobilized in specifically localized areas (21) of said support, which is in fluid communication with said labeled target molecules (13), possibly a carrier (12) for holding said support, a temperature control (16-17) system; the second part comprising:

an excitation light source (1), an optical system for directing and focusing an excitation light (2) from said excitation light source (1) on said support wherein the excitation light reaches the micro-array surface within an angle comprised between 45° and 135°, a detector (10) for measuring the electromagnetic light emission (7) from the bound target molecules in response to said excitation light in the presence of the solution containing the target molecules wherein the surface of emission for a localized area is comprised between about 0.1 $\mu m^2$ and about 10 $mm^2$, The apparatus may further comprise:

a storage system for storing the data of the different measurements for at least 4 localized areas of the support, a controller (11) repeating the steps of excitation, detection and storage at least two times for each localized area of the micro-array, a program for storing and quantifying at least 4 different target molecules present in solution using at least one measurement value for each said target.

DETAILED DESCRIPTION

Definitions

Figure 1:
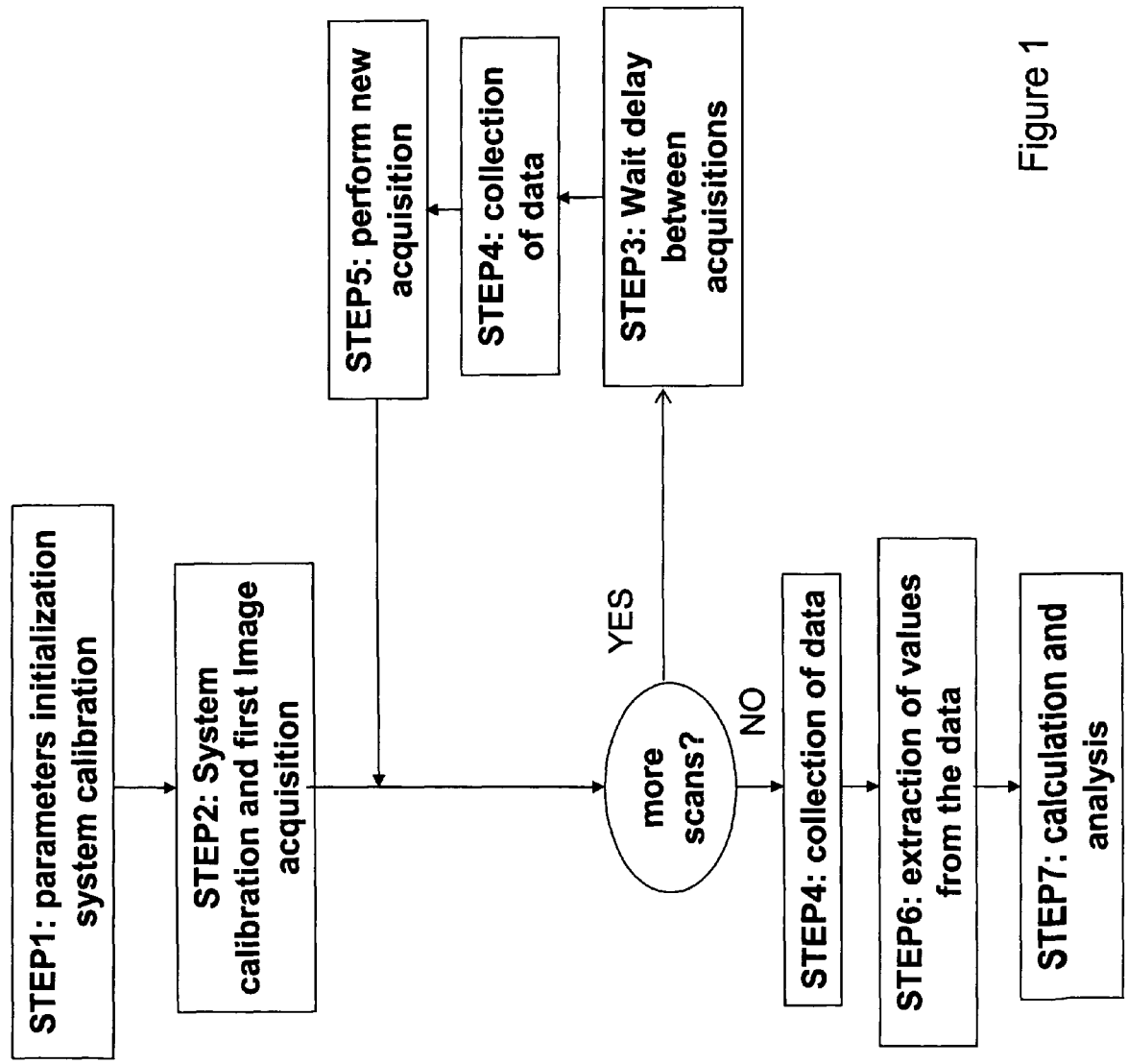
FIG. 1: Flowchart describing a specific embodiment in which real-time apparatus is controlled by a programmable computer.

In the context of the present application and invention the following definitions apply:

The term "real-time" refers to the time frame/period of a process to occur. The information or data of the process are monitored with time. In the context of micro-array, real-time refers to follow the binding reaction between the capture and target molecules for which the signal is detected and diagnosed with time. The data of the process are acquired either at predetermined timing or in a continuous way also called on line detection.

The "target" and "capture" molecules may be synthetic or natural molecules selected from the group consisting of nucleic acids, proteins, antibodies, saccharides, lipids, peptides, lectins, catalysts, receptors, agonists or antagonists of receptors, fluorophores, chromophores, chelates, haptens, ions, molecules having different chiral structures, new synthetic chemical macro-molecules obtained by combinatorial chemistry or other functionalized macrostructures, portions or a combination thereof.

As used herein, "capture molecule" refers to a molecule, or complex or combination thereof, that is capable of specifically binding to one target molecule, or to a family of target molecules, or to one or more member (s) of a plurality of target molecules, or portion(s) thereof. The capture molecules are preferably nucleic acids or proteins, which are either synthesized chemically in situ on the surface of the support or laid down thereon. Nucleic acid binding is achieved via base pairing between two polynucleotides, one being the immobilized capture molecule and the other one the target to be detected. Protein binding is best performed using antibodies specific for the capture of a given polypeptide or protein. Part of the antibodies, or recombinant proteins incorporating part of the antibodies, typically the variable domains, or other proteins or peptide or nucleotide can also be used as capture molecules for as long as they specifically recognized some given proteins of polypeptides.

The terms "nucleic acid, micro-array, probe, target nucleic acid, bind substantially, hybridizing specifically to, background, quantifying" are as described in the international patent application WO97/27317, which is incorporated herein by way of reference.

The term "nucleotide triphosphate" also called dNTP refers to nucleotides present in either as DNA or RNA and thus includes nucleotides, which incorporate adenine, cytosine, guanine, thymine and uracil as bases, the sugar moieties being deoxyribose or ribose. Other modified bases capable of base pairing with one of the conventional bases adenine, cytosine, guanine, thymine and uracil may be employed. Such modified bases include for example 8-aza-guanine and hypoxanthine.

The term "nucleotide" as used herein refers to nucleosides present in nucleic acids (either DNA or RNA) compared with the bases of said nucleic acid, and includes nucleotides comprising usual or modified bases as above described.

References to nucleotide(s), polynucleotide(s) and the like include analogous species wherein the sugar-phosphate backbone is modified and/or replaced, provided that its hybridization properties are not destroyed. By way of example the backbone may be replaced by an equivalent synthetic peptide, called Peptide Nucleic Acid (PNA).

The term "polynucleotide" sequences that are complementary to one or more genes or to the genome sequence described herein, refers to polynucleotides that are capable of hybridizing under stringent conditions to at least part of the nucleotide sequence of said genes or genome or copy thereof. Polynucleotides also include oligonucleotides being of more than 2 bases but below 100 bases long which can be used under particular conditions. Such hybridizable polynucleotides will typically exhibit at least about 75% sequence identity at the nucleotide level to said genes or genome, preferably about 80% or 95% sequence identity or preferably more than 95% nucleotide sequence identity to said genes or genome. They are composed of either small sequences typically 15-30 base long or longer ones being between 30 and 100 or even longer between 100 and 800 base long depending on the specificity and sensitivity requirements for the assay.

As used herein, "protein" encompasses polypeptides, oligopeptides and peptides. As used herein, "antibody" includes immunoglobulin which is composed of two light chains and two heavy chains linked by disulfide bounds and also fragments, such as Fab, $(Fab)_2$, Fv or single variable region fragments (scFv). As used herein, the term "receptor" refers to a molecule that has an affinity for a given ligand. Receptors may be naturally occurring or synthetic molecules.

The term "homology" is intended to mean the degree of identity of one polynucleotide sequence to another polynucleotide sequence. There may be complete homology (i.e. 100% identity) between two or more polynucleotides. The degree of homology is calculated after alignment of the sequence and may be determined by any methods well known for a person skilled in the art.

"Micro-array" means a support on which multiple capture molecules are immobilized in order to be able to bind to the given specific target molecule. The micro-array is preferentially composed of capture molecules present at specifically localized areas on the surface or within the support or on the substrate covering the support. A specifically localized area is the area of the surface which contains bound capture molecules specific for a determined target molecule. The specific localized area is either known by the method of building the micro-array or is defined during or after the detection. A spot is the area where specific target molecules are fixed on their capture molecules and seen by the detector. A spot is the area where specific target molecules are fixed on their capture molecules and seen by the detector. In one particular application of this invention, micro-arrays of capture molecules are also provided on different supports as long as the different supports contain specific capture molecules and may be distinguished from each other in order to be able to quantify the specific target molecules. This can be achieved by using a mixture of beads having particular features and being able to be recognized from each other in order to quantify the bound molecules. One bead or a population of beads are then considered as a spot having a capture molecule specific of one target molecule.

The terms "background" or "background signal intensity" refers to hybridization signals resulting from non-specific binding, or other non specific interactions, between the labeled target nucleic acids and components of the polynucleotide micro-array (e. g. the polynucleotide probes, control probes, the micro-array substrate, etc.). Background signals may also be produced by intrinsic fluorescence of the micro-array components themselves. A single background signal can be calculated for the entire micro-array, or different background signals may be calculated for each target nucleic acid. In a preferred embodiment, the background is calculated individually for each spot, being the level intensity of the signal on the surface surrounding the spot and not bearing the specific capture molecule.

The target molecules are typically detected by detecting one or more "labels" attached to the target. The labels may be incorporated by any of a number of means well known to those of skill in the art, such as detailed in WO 99/32660, which is incorporated herein by way of reference. The label is either detected directly or by indirect method.

The target molecule is intended to mean a polynucleotide or protein present in the biological material of interest and to be detected. The term "biological material" includes within its meaning organisms, organs, tissues, cells or biological material produced by a cell culture.

The term stable (or constant) and controlled temperature means a temperature which is obtained by a controlled system being a temperature regulation device and which is stable enough to avoid target hybridization rate variation of more than 10% during the time course of a given measurement. Typical stable temperature is a temperature which do not vary by more than 5° C. and preferably by more than 1° C. for at least one min and better 5 min of time period or even better 60 min of time period or even 24 h.

The targets are the detected labelled molecules. They are obtained either after extraction or purification of the molecules of interest present in a sample being preferentially a biological sample. The targets are the molecules of interact themselves being labeled or a copy or an amplification of these molecules. They may incorporate or not a label during these processes. Target molecules also includes chemical or biological molecules which interact with proteins of polypeptides. Typical of chemical targets are ligands binding on their receptors.

General Embodiments

In the main embodiment, target and/or capture molecules are biological molecules being protein or nucleic acids or sugar. The capture molecules are attached preferably by covalent link on some parts of the surface of the support. In an alternative embodiment, the support contains a substrate on which are fixed the capture molecules. In another embodiment, the capture molecules are adsorbed on the support as long as they are not significantly released in solution during the detection method.

Deposition of the capture molecules on the substrate is preferentially done by physical means such as pin or "pin and ring" touching the surface, or by release of a micro-droplet of solution by methods such as piezo or nanodispenser. Alternatively, in situ synthesis of capture molecules on the substrate is one of the invention embodiment with light spacial resolution of the synthesis of oligonucleotides or polynucleotides in predefined locations such as provided by U.S. Pat. Nos. 5,744,305 and 6,346,413. The capture molecules are preferably present in defined locations on the substrate.

In a preferred embodiment the localized area for the detection of a target has a surface comprised between 1 $\mu m^2$ and 1 $mm^2$.

In one main embodiment, target molecules are labeled polynucleotides present in solution and their binding on their specific capture molecules present in different localized areas of the micro-array is followed by monitoring with time electromagnetic light emitted by the micro-array bound target with at least 2 measurements being made for each of the targets to be detected.

In a preferred embodiment, thickness of the solution being in contact with the micro-array is constant above all the localized areas.

In still another embodiment, the difference of thickness of the solution being in contact with two localized areas or spots of the surface is lower than 100 micrometers and even lower than 10 micrometers and even lower than 1 micrometer.

In another embodiment, the thickness of the solution being in contact with the micro-array is changed between two measurements and the thickness of the solution being in contact with the micro-array is constant for two measurements.

In another embodiment, the target molecules are obtained from mRNA present in a biological sample. The mRNA is copied into cDNA and the detection of the cDNA is followed online on the micro-array.

In another embodiment the cDNA are obtained from the mRNA using polydT polynucleotide sequence having a T7 polymerase binding sequence. The T7 polymerase is used to copy the cDNA into RNA sequence as described in WO9710365. The RNA molecules are fragmented randomly preferentially by heating into alkaline solution or in the presence of magnesium ions. One at least of the RNA fragments is then detected online on the micro-array by one of the method described above. The cDNA are polynucleotides having sequence of 100 bases or longer.

In another embodiment the target molecules are obtained from the DNA present in a biological sample. The DNA is extracted from the sample and amplified preferably by PCR and the amplicons are detected online by their fixation on their specific capture molecules. In one particular embodiment, the target molecules are homologous nucleotide sequences which are detected and/or quantified online on micro-array after amplification of genomic DNA by consensus primers as described in WO0177372.

In another embodiment the amplified DNA are cut into smaller polynucleotide fragments preferentially either by restriction enzymatic digestion, by treatment with DNase or by chemical cut. At least one DNA fragments per target is then detected online on the micro-array by one of the method describes here above.

In another embodiment, the method of the invention is used for the determination of optimal hybridization condition of one target present in solution and preferentially of several targets present in the same solution.

In another embodiment, the method of the invention is used for the determination of high binding efficiency of a target molecule on its specific capture molecule while having a very high discrimination of fixation with nucleotide sequences differing by at least one nucleotide from the target sequence.

In another embodiment, the invention is used to differentiate between two nucleotides sequences which differ by at least one nucleotide. The invention is particularly useful to determine the optimum condition for hybridization while having a specific binding of the targets on their capture molecules. The optimum conditions are quickly found by testing various stringency solutions or/and temperature of incubation and recording in a short period of time the signals given by the targets to be discriminated. The conditions where the discrimination is higher than 10 and preferably higher than 20 and even preferably higher than 100 or more and which still give significant signal for the required targets is than selected for further studies. More rigorously, the best conditions are given by the crossing point of the curve giving the yield of hybridization in % of the maximum with the curve giving the discrimination in % of the maximum expressed by the variable used in the experiments, mainly the T° or the stringency.

In a preferred embodiment, the method of the invention is used for optimizing hybridization condition for the SNP detection in a target sequence and/or quantification. In another embodiment, the method of the invention is used for optimizing hybridization and detection conditions of SNP in multiple target sequences possibly present in the same solution.

In one main embodiment, target molecules are labeled oligonucleotides having a length of between 10 and 99 nucleotides present in solution and their binding on their specific capture molecules present in different localized areas of the micro-array is monitored with time with at least 2 measurements being made for each of the targets to be detected.

In the preferred embodiment, the polynucleotides being used as capture molecule are between 10 and 1000 nucleotide long and preferably between 100 and 400 nucleotides long. For specific binding of homologous sequences possibly present in the same sample, the polynucleotide capture molecules contain a spacer according to the patent WO0177372. Specific binding of homologous sequences or SNP possibly present in the same sample, are obtained using capture molecules having a specific part being between 10 and 30 nucleotides.

In the preferred embodiment, the polynucleotides being used as capture molecules are present on the micro-array localized area at a density superior to 10 finoles, and preferably 100 finoles per $cm^2$ surface of the solid support.

In another embodiment, target molecules are labeled proteins present in solution and their binding on their specific capture molecules present in different localized areas of the micro-array is followed by monitoring with time the electromagnetic light emitted by the micro-array bound target with at least 2 measurements being made for each of the targets to be detected.

In still another embodiment, the targets are antigens being detected by the binding on capture molecules, which recognize specifically the different antigens to be quantified, among the specific capture molecules are antibodies or parts thereof or molecules having complementary structure to the antigen such as the aptamers or other proteins.

In still another embodiment, the targets are the antibodies being present in the solution to be quantified and the capture molecules being their respective antigens, or part of them or epitopes. In still another embodiment, the targets are proteins or ligands for which a specific receptor is present as capture molecule on the micro-array; in the reverse situation the proteins or ligands are used as capture molecules and the receptors are detected as targets.

In still another embodiment the target molecules are transcriptional factors, which recognized specific DNA sequence being immobilized as capture molecules on the micro-array.

In the preferred embodiment, the proteins being used as capture molecules are deposited onto the support in an amount sufficient for providing an adequate assay system, generally in an amount of from about 2 to 10 ng/µl, preferably between 3 and 6 ng/µl of spotting solution.

The support as such may be made from any material conventionally used for this purpose and is preferably selected from the group consisting of glasses, electronic devices, plastics, silicon supports, silica, metal or mixtures thereof prepared in format selected from the group of slides, discs, gel layers and/or beads. In a preferred embodiment, the support is glass.

In another preferred embodiment, the support bearing the capture molecules has a 3 dimensional porous structure. Conventional glass slides have less than 60% silicon dioxide on their surface. This inherently limits the amount of chemical bonding available on the surface. Porous material exhibits increased loading capacity of capture molecules. Typical porous supports are gel pads, fused-fiber matrix, fibrous polymer matrix. The micro-array can be constructed entirely of the porous material, or can comprise a layer of porous material mounted on top of a flat surface such as glass, plastic, or metal.

In another embodiment capture molecules are present on different supports being preferentially beads with chemical or physical characteristics for their identification with a specific capture molecule.

In still another embodiment, the support bears several micro-arrays separated by physical or chemical boundaries. In a preferred embodiment, the support has a multi-well format. Examples for physical barriers are wells, e.g. the support being a 96, 384, 1536 multi-well plate, having separated wells onto which capture molecules maybe spotted individually. 384-well and 1536-well plates are available from BD Falcon for cell based assays (Merck Eurolab sa, Leuven, Belgium) or from Nunc A/S (Roskilde, Denmark). 6144 format microtiter plates are available from Parallel Synthesis Technologies Inc. (PSTI, Menlo Park, Calif., USA). Other physical barriers are tubes such as 96, 384, 1536 or even 6144 tubes deposit at the surface of the support. Tubes are similar to the well formats but do not have a plain bottom sot that when deposit on the surface of the support, they create localized areas isolated from each other. An example for a chemical barrier is e.g. described in DE 0019949735A1, where defined areas within a hydrophobic surface are provided with hydrophilic anchors allowing the precise location and confinement of capture molecules on a solid support.

The micro-array according to this invention contains between 4 and 100.000 spots per $cm^2$ and preferably between 20 and 1000 spots per $cm^2$, each spot being the localized area for one capture molecule. In a preferred embodiment, the micro-array contains more than 20 different capture molecules and less than 1000.

Detectable labels suitable for use in the present invention include any composition detectable by any methods based on the detection of electromagnetic light emission.

The target molecules may be labeled with a fluorescent dye. The fluorescent label is incorporated into the target by enzymatic or chemical reaction. Typical enzyme reaction includes the incorporation of labeled nucleotide triphosphate into the target. Alternatively, a primer labeled at its 5'-end with a fluorescent dye is incorporated into the target while copying or amplifying DNA or RNA. Fluorochromes are also be incorporated into the targets by chemical reaction such as the reaction of fluorescent dye bearing a N-hydroxysuccinimide (NHS) group with amines or sulfhydryl groups of the targets. Useful fluorescent dyes in the present invention include cyanine dyes (Cy3, Cy5, Cy7), fluorescein, texas red, rhodamine, green fluorescent protein. Patents teaching the use of such labels include U.S. Pat. Nos. 3,817,837; 3,850, 752; 3,939,350; 3,996,345; 4,277,437; 4,275,149; and 4,366, 241. In a preferred embodiment, the fluorescent dye is cyanin 3.

Some fluorescent labels may be of particular interest, such as nanocrystals particles having fluorescent properties. The most common one are the Quantum dots proposed by Han et al. (Nature Biotechnology 19, 631-635, 2001). They are fluorescent and do not bleach with time or with illumination. Their stability makes them particularly suitable for the use in continuous reading as proposed in this invention. Also, they contain metals which confer to these particles specific properties so that other methods than the fluorescence can be used to follow their attachment on the capture probes. The thermal heating of these particles is one of the parameters that may be followed with time. The fact that the metal absorbed the energy of a light beams preferably a laser and induce a heating of the particle has been used as a basis for the detection of low density gold particle on a support and even single particles are detected (Boyer et al Science, 297, 1160-2002). The method is called the Photothermal Interference contrast.

Another technology for the direct measurement of nanoparticles is the Rayleigh Scattering. This method is based on the use of a light beam adapted in order to obtain an oscillation of the electrons in the metal particle so that an electromagnetic radiation is obtain from the particle which can be detected. (Stimpson et al., Proc. Natl. Acad. Sci. USA 100 (2003), 11350-11353) (real-time detection of DNA hybridization and melting on oligonucleotide arrays by using optical wave guides) The method is lacking sensitivity for the applications on biological samples.

Alternatively, Raman scattering and the surface plasmon resonance may applied in the present invention, which technique has been extensively used for the detection of antibody/antigen binding but are also well suited for the multiparametric measurement of the arrays and for the required sensitivity on biological samples. (Thiel et al., Analytical Chemistry, 69 (1997), 4948-4956).

In another embodiment, quartz crystal microbalances may be applied, which are now sensitive enough that they can measure changes of mass lower than nanogram (cf. Caruso et al., Analytical Chemistry 69 (1997), 2043-2049). This is one proposal for micro-array detection in real-time.

Cantilevers are another option for the detection of DNA on micro-arrays. (McKendry et al. Proc. Natl. Acad. Sci. USA, 99 (2002), 9783-9788).

Also, another technology is the electrical detection of the nanoparticles which takes into account their metal properties. The electrochemical detection was first applied but with low sensitivity. The more advanced and sensitive method is the detection by differential pulse voltametry (Ozsoz et al., Analytical Chemistry 75 (2003), 2181-2197).

The resistivity and the capacitance properties of the metal are also one of the best properties to be detected on electronic chips. The presence of a metal between two electrodes will induce a change of resistivity and of capacitance; The detection of the DNA or proteins is then observed when the capture molecules are present on one of the electrode (Moreno-Hagelsieb et al Sensors and Actuators B-Chemical, 98, 269-274, 2004). The capacitance assay of the gold labelled DNA has been described by Guiducci et al. ESSDERC 2002. Since electronic chips can be made of several plots, different targets may be detected on different plots and the change in the resistivity or in the capacitance may be recorded. If the methods have not yet been able to produce reliable and sensitive detections as required by the biological samples, it is, however, predicted that some of them will succeed to fulfil the requirements for the real-time detection.

These methods may be advantageously used for the detection of the DNA together with its amplification as proposed in the invention.

In a particular embodiment, the target molecules bear a label which is recognised by a fluorescent molecule and which is detected online on the micro-array. Typical nucleotide label is the biotin which is recognised by streptavidin or antibiotin antibodies bearing a fluorescent dye.

Embodiments on Advantages

In a preferred embodiment, the method is used for the detection of several target molecules being present in concentrations between about 0.0001 and about 1000 nM in the detection solution and preferably between 0.001 and 10 nM.

In a preferred embodiment, the binding reaction, detection and quantification are performed in an integrated apparatus. They do not necessitate handling of the reaction method such as washings or addition of reagent for obtaining a staining or a detectable signal.

In a preferred embodiment, the quantification is obtained with a high precision, the standard deviation of the measurements being lower than a factor of 2 and preferably of 5 compared to a single measurement performed at one time during the reaction.

In another preferred embodiment the total time of the reading of the signal necessary in order to obtain a quantification of the targets with the same precision is reduced by a factor of 2 or even 5 compared to the one time detection method.

In another preferred embodiment the signal values for the quantification calculation of the different targets are taken in a time frame where they are proportional to the concentration of the targets in the solution. The time frame is different for the different targets and depends on their concentration in the solution.

One of the characteristic of the invention is the acquisition of a kinetic value for the binding of a target on its capture molecule which is proportional to the concentration of said target in solution. Kinetic value is typically a coefficient of reaction rate being of zero, first or second order or more complex. In a preferred embodiment, the reaction conditions are chosen such as the initial rate is of first order for all the targets to be assayed and of zero order for the capture molecules. The concentration of the bound target molecule (x) at a given time is then given by the equation: $C(x)=k\,t$, with k being the kinetic coefficient for the targets and t the time of the reaction.

At the start of the reaction, the kinetic coefficient is proportional to the initial concentration (Ci) of target molecule.

In a preferred embodiment, the calculation of the concentration of a target present in solution is derived from the calculation of the kinetic coefficient of the signal appearance with time in the localized area to which the target binds in a specific manner.

In another preferred embodiment, the concentration of the target present in solution is calculated from the first order kinetic coefficient of the signal taken from at least 3 values taken with time in the localized area to which the target binds specifically.

In another embodiment, the concentration of the targets present in solution is calculated from the time necessary to reach a particular threshold of signal.

In an embodiment, the temperature during of the binding reaction has to be controlled and stable with a variation of the temperature lower than 5° C. and preferably lower than 1° C. during the two or more measurements performed with time.

In a further embodiment, the temperature is stable for at least 1 min, preferably between 1 and 5 min, more preferably between 1 and 60 min and even more preferably between 1 min and 24 h during the calculation period.

In another embodiment, the reading is performed between 1 min and 24 h.

In an embodiment, the method allows to detect targets having at least 4 and better 5 and even better 6 log concentration difference. In a further embodiment, the method allows to quantify targets differing by at least 4 and better 5 and even better 6 log concentration difference.

In a particular embodiment, the solution containing the target molecules is submitted to temperature cycles having at least 2 and preferably 3 different temperatures between two or more measurements. The number of cycles in preferably of 2 and more preferably more than 10 and even preferably more than 20 and preferably limited to 50 cycles. The measurement of the fixed target on the micro-array is performed preferably by at least two measurements performed in at least 1 and preferably in 5 and better 10 and even better in 20 or more cycles.

In the preferred embodiment at least two measurements are made at each cycle and the level of the detection is expressed for each of the tested target with the cycle number. The quantification of the targets is then obtained by comparison of the cycle number necessary for reaching a threshold. In the preferred embodiment at least one internal standard having known concentration is incorporated into the solution in order to correct for the quantification. The absolute amount of targets is than calculated in reference to the data obtained with the internal standard. Preferably 3 or more internal standards at different concentrations are incorporated into the target solution and the quantification of the targets is calculated by reference of the standard curve obtained with these internal standards.

In one particular embodiment, the online measurement is performed at one fixed temperature during the cycle. In another embodiment, the online measurement is performed after the last cycle.

In a preferred embodiment, the solution contains a DNA or a RNA polymerase, the required dNTP or NTP and the necessary salt buffer and reagents in order to allow a polymerase to copy DNA or RNA.

In an embodiment, the solution contains 5' end labeled oligonucleotides or primers which serve as anchors for a polymerase to copy the target sequences to be detected on the micro-array.

In another embodiment, the solution contains labeled dNTP or NTP which are incorporated by the polymerase into the target sequences to be detected on the micro-array.

In a preferred embodiment, the temperature cycles and the reaction conditions are those which produce a PCR. In a another embodiment, the temperature cycles and the reaction conditions are the one of a reverse transcription of RNA into cDNA.

In a preferred embodiment, the polymerase used for PCR on micro-array is the hot Master (5 Prime, Colo., USA) which works at 62° C. In a preferred embodiment the steps of annealing, elongation and hybridization on the micro-array are performed at the same temperature which is comprised between 60 and 68° C. In such embodiment, the real-time detection assay is performed together with the elongation step and even better during the annealing and elongation steps.

In one preferred embodiment, the capture molecules present on the micro-array are complementary to at least one part of the sequence of the copied or amplified target sequences present in solution.

In an embodiment, the capture molecules are elongated by the polymerase and are in the same time hybridized with the amplified products which accumulate in solution during the cycle. In one embodiment, the elongated capture molecules are labeled and are detected online during the cycle or at the end of the cycle. In this case, elongation is preferably performed in the presence of labeled dNTPs.

In an embodiment, the capture molecules are preferentially either elongated by the polymerase or hybridized with the amplified products which accumulate in solution during the cycle.

In a preferred embodiment, the hybridization is favoured over the elongation by using capture probes which are not capable of being elongated. In this case, capture molecules may include a base terminator or long stretch of identical bases at their 3' end such as polyA. Alternatively, the capture molecules may be immobilized on the support by their 3' end, the free 5' end being not able to be elongated by the polymerase.

In another embodiment, the elongation is favoured over the hybridization by performing PCR in the presence of one primer in excess and a reduced amount of the other primer.

In an embodiment, the micro-array is in contact with reagents for carrying out the copy or amplification of one or more target sequences. In a preferred embodiment, the target sequences are homologous sequence copied or amplified with consensus primers. In a preferred embodiment, each capture molecule of the micro-array is directed against a particular homologous target sequence which has been amplified with consensus primers in the presence of one or more other homologous sequences.

Embodiments on Apparatus

The apparatus used in order to perform the method according to the invention contains two different parts.

The first one contains the incubation system which provides the conditions necessary for the binding reaction of the targets onto their capture molecules. Preferably the first part contains a temperature control system for regulating and controlling the temperature during the binding reaction.

In a preferred embodiment, the temperature regulating device is selected from the group consisting of a controlled peltier, a micro-thin wire heating element laid in a pattern between optical grade polyester sheets like Thermal-Clear™ transparent heaters from Minco, or fluidic system circulating externally temperature regulated fluid.

In a preferred embodiment, the temperature regulating device is mounted on a carrier holding the support. The temperature regulating device is preferably positioned between the carrier and the support.

In another embodiment, the temperature regulating device is mounted on the support and is not in contact with the carrier.

In a preferred embodiment, the incubation system provides conditions so that the thickness of the solution being in contact with the micro-array is constant above all the arrayed spots or localized areas. The difference of thickness between two spots or localized areas of the arrayed surface is preferably lower than 100 micrometers and even lower than 10 micrometers and even lower than 1 micrometer.

In another embodiment, the incubation system provides conditions for the thickness of the solution being in contact with the micro-array is changed between two measurements.

The first part of the apparatus also preferably contains a mixing or agitation system for the liquid to be moved inside the reaction chamber and increase the reaction rate. In a preferred embodiment, the mixing is performed by movement of the liquid by physical means such as pump, opening and closing valves, electrostatic waves or piezoelectric vibrations.

The second part contains the detection system required to detect the light emission from the target bound to their corresponding capture molecules. A light source generates a beam of light to excite the labeled targets on the support. In the preferred embodiment, the detection part has to be settled in such a way as to obtain the same detection efficiency on the overall surface covered by the micro-array to be analyzed.

In a preferred embodiment, the excitation light is a laser beam preferably having a wavelength of about 532 nm delivered at a power of about 15 mW with a divergence that may be below 1.2 mrad. In another embodiment, the detection system contains 2 or even 4 lasers.

In a preferred embodiment, the laser beam (2) generated by the light source (1) is nearly collimated and nearly Gaussian. An exchangeable excitation filter (4) is used to collect only the wavelengths of interest. An additional filter wheel (3) is preferably placed and used as an attenuation filter to precisely regulate the laser power. This filter wheel is shaded differently at variable know absorption levels. A lens (5) that may be anti-reflection coated is used for focusing the laser beam on the support (15). The distance between the light source, the lens and the support is variable to allow focusing.

Thereafter, the light passes through a dichroic mirror or beam splitter (6). This mirror pass light having a wavelength lower than about 530 nm, but reflect light having a wavelength greater than 560 nm. Consequently, the 532 nm light coming from the laser is passed through the dichroic mirror to the support. The light then passes through a reaction chamber (14) and the fluorescent marked sample (13) and reaches the support (15), where bound labeled target are excited and emit fluorescence at about 560 nm.

Emitted light (7) is then focused through a focusing lens (9) to a photomultiplier tube (10) for detecting the number of photons present therein.

In a specific embodiment, an additional emission filter (8) that transmits light having a wavelength greater than about 550 nm is added. Thus, photomultiplier tube (10) detects substantially only fluoresced light. The Photomultiplier tube generates a pulse for each photon detected. Each of these pulses is amplified and converted to an electronic signal by photoelectric effect. A data acquisition board or controller (11) then collects the resulting signals. The controller includes a temperature controlling device.

After data are collected from a region of the substrate, the carrier (12) moves the support so that excitation light is directed to a different region on the support (15). The process is repeated until all regions on the substrate have been scanned. In another embodiment the support is fixed and the light excitation beam is moved from one part to the other on the surface of the support. In still another embodiment, the overall micro-array is illuminated and the light emission from each localized area is detected.

In one embodiment, the support itself is a carrier.

In a preferred embodiment, the data are stored and treated for calculation of the amount or concentration of the different target molecules in solution and in the original biological sample. Data storage and data treatment are preferably performed using a programmable computer which is integrated in the apparatus of the invention. Data treatment can be performed at any time after data storage.

In one embodiment, the support is moved relative to the detection system during the reading. The support moves relative to the excitation light to allow the reading of different regions of the support. The excitation light may be fixed or moved in one direction to scan the support.

In an alternative embodiment, the support is moved relative to both the incubation and detection systems. During the incubation, the support is in contact with the temperature control system (incubation position). When a reading has to be effected, the support is moved from the incubation system to the detection system (reading position). During the reading, the support is either moved relative to the excitation light or is fixed. After the reading the support turns back to its initial position. One advantage of moving the support relative to the incubation part during the reading is to avoid deleterious effect of the heating device on parts of the detection system.

In another embodiment, the two parts of the apparatus are fixed and work together with no movement of the solid support relative to the incubation and detection parts. A typical detector used in this context is a CCD camera which is able to take a picture of the whole micro-array.

The flowchart of FIG. 1 describes a specific embodiment in which real-time apparatus is controlled by a programmable computer which controls the parameters of the two parts of the system. The scanner is comparable to a Genepix 4200A scanner from Axon coupled with the scriptable Genepix 5.1 software from Axon.

At STEP 1, the user is prompted to fill in the required parameters, such as: resolution, voltage of the PMT, laser power, number of scans, time between scan, scan area. Temperature of the substrate is set separately on the heating system that can be a peltier device mounted on the substrate.

Parameters of the System:

The resolution defines the pixel size. Generally, the pixel size is chosen which results in more than 1 pixel per localized area and preferably between 10 and 100. Setting a too high resolution generates an overload of data while having a too low pixel size generates low quality results.

The PMT voltage multiplies the detected signal. Increasing the laser power will increase the photon count in each pixel.

The "number of scan" parameter corresponds to the number of times the user wishes to scan the substrate while the "time between scans" parameter controls the amount of time to wait before commencing a subsequent scan. In this manner, the user may perform a series of scans to follow the kinetics of the reaction.

Scan area parameter corresponds to the size of the substrate to be tested.

The temperature parameters control the temperature at which detection is performed. Temperature may vary depending on the type of polymers being tested. Preferably, testing is done at a temperature that produces maximum binding affinity while minimizing mismatches.

The system is then initialized: carrier is moved to home position while laser power is checked. At STEP 2, first scan is performed and the fluorescence emitted on the selected region comprising the micro-array of the substrate is collected. The JavaScript callback is launched when the scan is done (STEP 3). If the number of scans to be done is not reached, then the program waits for the delay asked by the user. Then the image is saved at STEP 4, and if required a new scan is performed (STEP 5). The JavaScript callback allows the loop to be continued. In STEP 6, values are extracted from the data and in STEP 7; the calculation and analysis are performed. For this purpose a grid which contains the number of rows and columns of the micro-array to be measured is positioned on the micro-array. The grid is composed of circles which diameter in pixels correspond to the diameter of the spots to be quantified. The diameter is depending on the resolution chosen for the scanning. The means of the pixels intensity inside the circle gives the spot signal. This signal is then calculated for each time and plotted versus the incubation time. STEP 6 is preferably performed by importing the scanned 16-bit images to the software, 'ImaGene4.0' (Bio-Discovery, Los Angeles, Calif., USA), which is used to quantify the signal intensities.

Algorithm Linked to FIG. 1

```
<html>
<head>
  <style type="text/css">
     @import url(GenePix_Style_Base.css);
  </style>
  <title>Example Automation</title>
</head>
<body marginheight="0" marginwidth="0" topmargin="0" leftmargin="0">
<!-- HTML Layout portion -->
<p>
<table width=600 border=0 cellspacing=0 cellpadding=5>
   <tr class="title">
      <td>
        <p class="heavy">Real-time scanning: allow scanning multiple time the
same sample at constant time intervals without any user intervention
      </td>
   </tr>                          // STEP 1: USER PARAMETERS
   <tr>
     <td class="underline instructions">
         <p>PMT: <input type=text size=2 name=setpmt value="700">
         <p>Resolution: <input type=text size=2 name=setres value="40"> µm
         <p>Scan interval: <input type=text size=2 name=interval value="120">
(s)
         <p>Scan numbers: <input type=text size=2 name=snumber value="10">
<p>
<input type=checkbox size=5 name=saved value="10">Save images ?
         <p>Images  directory:  C:\Documents  and  Settings\user\desktop\<input
type=text size=20 name=ipath value="">
     </td>
   </tr>
   <tr>
     <td class="underline instructions">
         <input type="button" value="Prescan" onclick="GenePix.PreviewScan( )">
         <input type="button" value="Start scanning" onclick="startscan( )">
     </td>
   </tr>
   </tr>
</table>
<!-- Scripting portion -->
<script language=vbscript>
//
++++++++++++++++++++++++++++++++++++++++++++++++++++++++++++
++++++++++++++++++++++++++++++++++++++++++++++++++++++++++++
+++++
Option Explicit
Dim GenePix
Dim Scanner
dim i     // PMT VALUE
dim j     // RESOLUTION (µm)
dim k     // SCAN INTERVAL (s)
dim n     // NUMBER OF SCANS
dim c     // COUNTER
dim s     // IMAGES PATH
dim t1    // TIMER
// This procedure is launched by pressing on the start scan button
++++++++++++++++++++++++++++++++++++++++++++++++++++++++++++
++++++++++++++++++++++++++++++++++++++++++++++++++++++++++++
+++++
sub startscan( )                   // STEP 2
c=0
Set GenePix = window.external      // declares scanner object
Set Scanner = GenePix.Scanner
GenePix.DiscardImages( )           // clears the display
call InitializeCallbacks( )        // defines the Javascript callbacks
i=cint(setpmt.value)               // sets the PMT value
j=cint(setres.value)               // sets the resolution value
k=cint(interval.value)             // sets the time interval between scans
n=cint(snumber.value)              // sets the number of scans
s=cstr(ipath.value)                // sets the path of the images
Scanner.PixelSize=j
Scanner.PMT(0)=i
t1=timer( )                        // sets the time 0
GenePix.DataScan                   // starts the first scan
end sub
// Saves the image and launches a new scan
++++++++++++++++++++++++++++++++++++++++++++++++++++++++++++
++++++++++++++++++++++++++++++++++++++++++++++++++++++++++++
+++++
```

```
                                                      -continued
Function ScanDone( )                          // STEP 4
if saved.checked=true then                    // saves the image
GenePix.SaveImages "C:\"  & s & "\RT-"& cstr(formatnumber(timer( )-t1-k,0))
&" s.tif", "", &h008000
end if
GenePix.DiscardImages( )                      // reinitializes the display
c=c+1                                         // counts the number of scans
if c<n then                                   // STEP5: and if necessary,
GenePix.DataScan                              // launches a new scan
end if
End Function
</script>
<script language="JavaScript">
// This function is called after a scan is done
+++++++++++++++++++++++++++++++++++++++++++++++++++++++++++++++
+++++++++++++++++++++++++++++++++++++++++++++++++++++++++++++++
+++++
function waitjs( )                            // STEP3
{
if c<n then                                   // if more scans have to be done,
setTimeout("ScanDone( )",k*1000);             // pauses the program during the
                    time
else                                          // interval and calls the ScanDone
function
Scandone
End if
}
// Javascript callback: defines which function has to be run after which event
+++++++++++++++++++++++++++++++++++++++++++++++++++++++++++++++
+++++++++++++++++++++++++++++++++++++++++++++++++++++++++++++++
+++++
function InitializeCallbacks( )
{
GenePix.OnScanDone = function ( ) { waitjs( ); }
}
</script>
</body>
</html>
```

Figure 2:
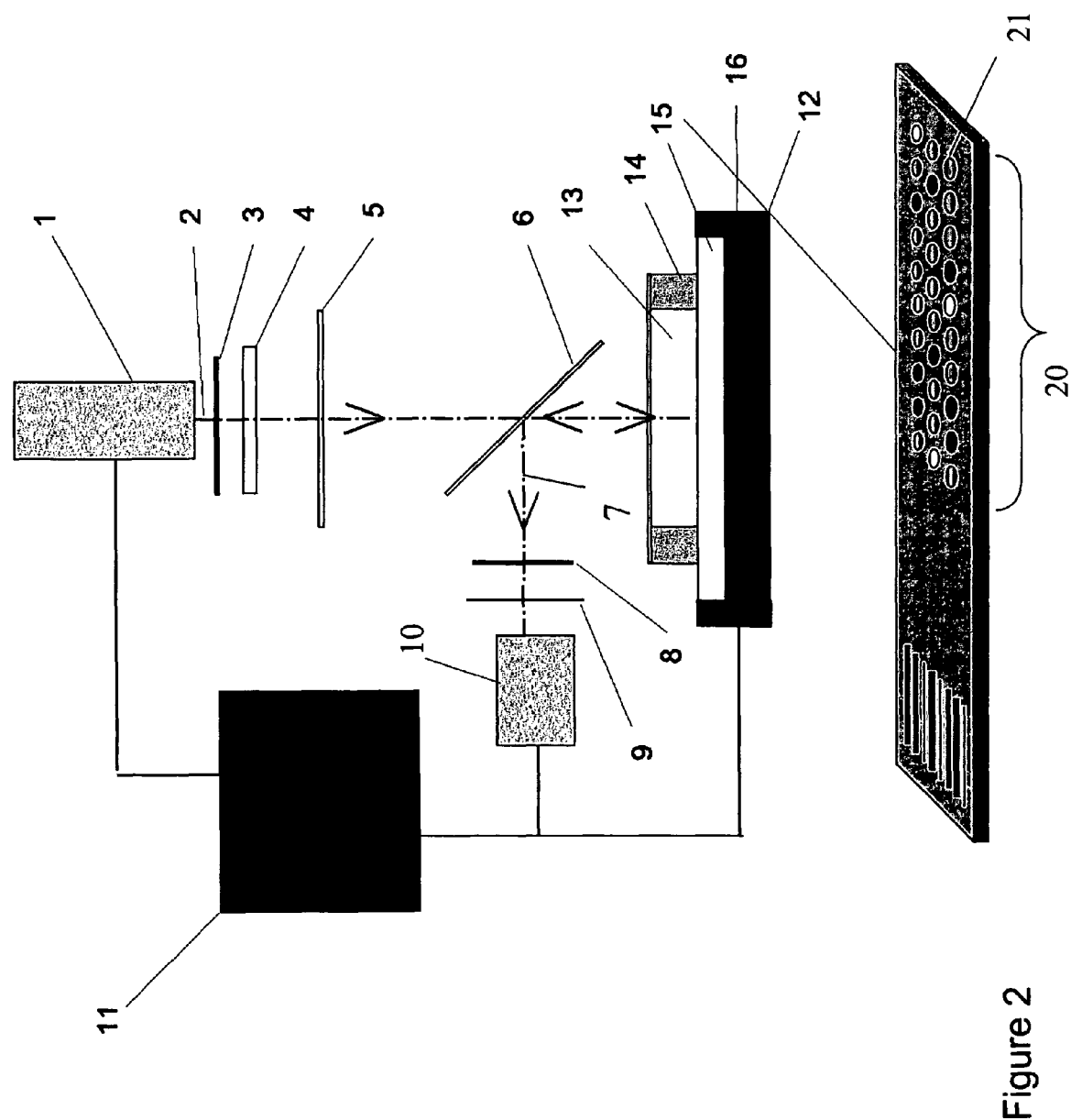
FIG. 2: General scheme of the integrated apparatus comprising the support (15) a carrier (12), the temperature regulating device (16) and the detector (10).

FIG. 2 represents one embodiment of the invention in which parts of the two processes are present in the same compartment. The two processes are performed in the integrated system as long as the technical parts (necessary for having the specifications) are compatible with each other. The light source (1) is directed on the surface of the support (15) opposite to the surface in contact with the thermostatized carrier (12). The controller (11) includes a temperature controlling device.

In preferred embodiment, the excitation light (2) reaches the micro-array surface within an angle comprised between 45° and 135°, preferably between 60° and 120°, even more preferably between 80° and 100°. The light excitation is a direct excitation of the labeled target and do not use the internal reflexion of the light such as provided by the evanescent waves.

Figure 3:
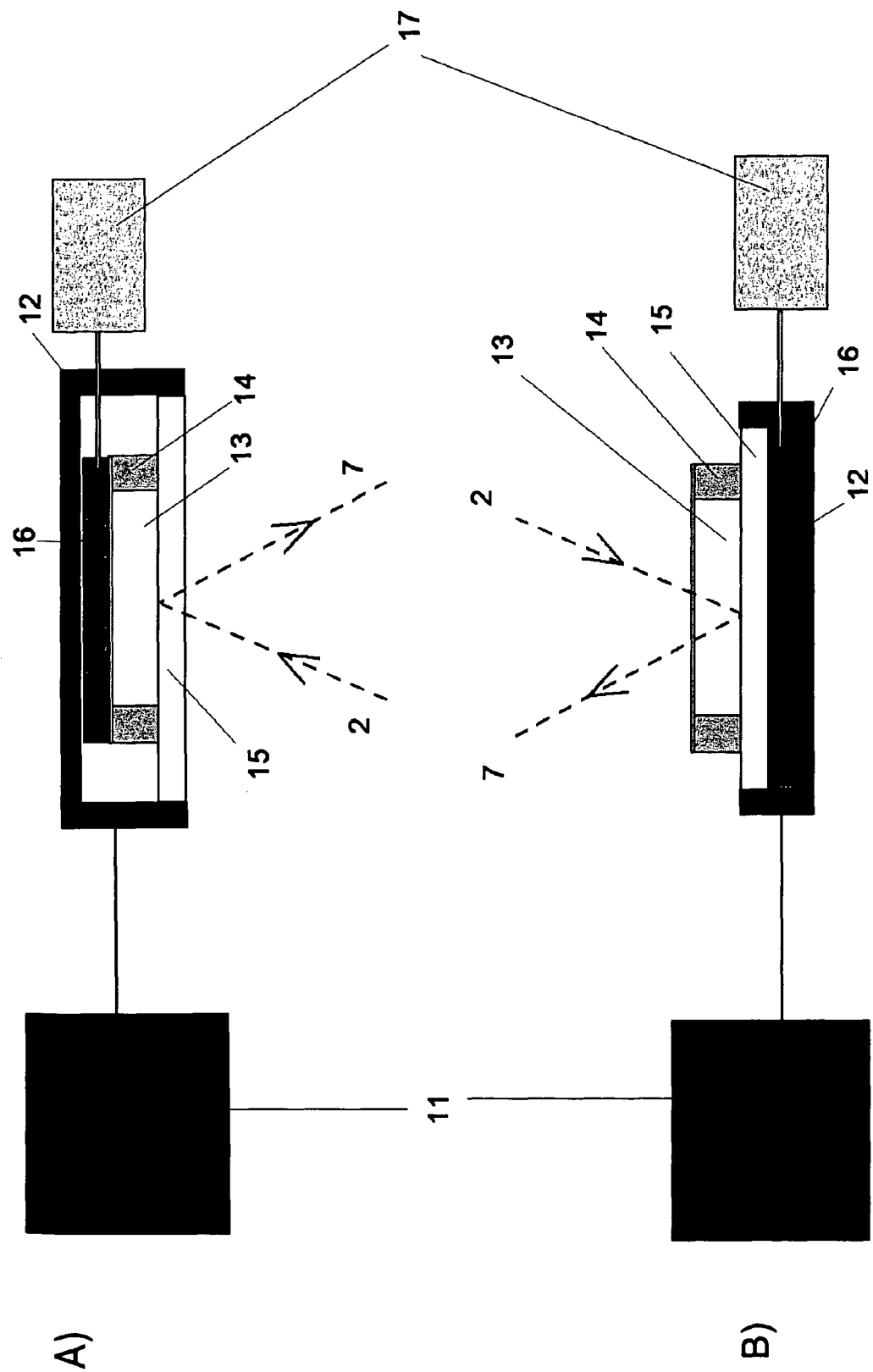
FIG. 3: General scheme of the apparatus where the thermostatized carrier is physically separated from the detector. The figure presents the carrier part of the apparatus with light excitation reaching the micro-array either through the solution (B) or through the support (A).

FIG. 3 represents another embodiment of the invention in which the two processes are physically separated in two different parts of the apparatus. Some parts are moved: either the part of the machine and the support (15) is static or the support moves from one part to the other of the apparatus in order to be in the position to perform one of the two required processes or the target solution (13) moves either in block or in part, e.g. to be heated in one part and to react in an other part, or to perform the detection. The reading excitation light (2) is either directed and focused on the support (15) without crossing liquids (A) or through liquids (B) depending on the side of the support, which is illuminated.

In one embodiment, the excitation light (2) is directed and focused on the support without crossing liquids.

In another embodiment, the excitation light (2) is directed and focused on the support through liquids.

Figure 4:
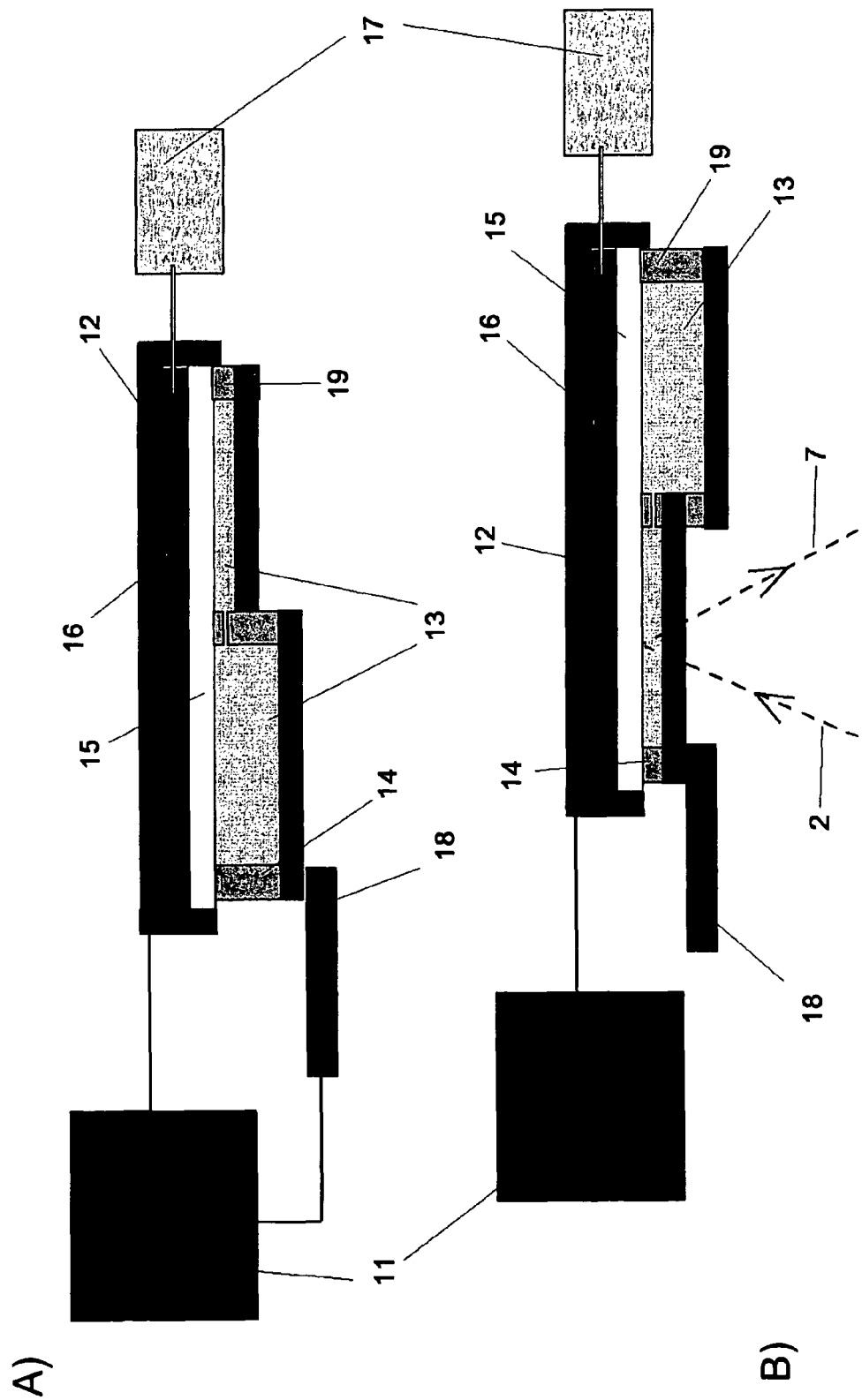
FIG. 4: Scheme of the apparatus carrier comprising a reservoir (19) for liquid transfer during reading. During the binding reaction, the reaction chamber is full and the reservoir is empty or nearly empty (A). During the reading of the micro-array, the thickness reaction chamber (14) is reduced and the reservoir is full (B).

FIG. 4 represents still another embodiment of the invention in which the carrier (12) comprises a fluid mixing system. In a preferred embodiment, the reaction chamber (14) where the binding between target and capture molecules occur is in fluid communication with a reservoir (19). The carrier (12) and temperature regulating device (16) may be separated from the temperature controlling device (17). The controller (11) may also operate a device (18) to compress the reaction chamber (14). The reaction chamber (14) is compressed by the device (18) allowing the fluid to fill the reservoir (19). The succession of compression and depression of the chambers allow the mixing of the solution. The reading of the micro-array is preferably performed when the reaction chamber is compressed. Two readings are made with the same compression.

In another embodiment, the liquid present in the reaction chamber is moved to the reservoir (19) by insertion of a glass slide in the reaction chamber (14).

In another embodiment, during the reading of micro-array, the thickness of liquid in the reaction chamber is comprised between 0.1 microns and 500 microns and preferably between 10 and 100 microns.

In another embodiment, during the reading of micro-array, the thickness of liquid in the reaction chamber as compared to the reservoir is smaller by a factor of between 2 and 100 times.

EXAMPLES

Example 1

Real-Time Hybridization of the Same Concentration of Six Different Polynucleotides on Complementary Capture Molecules of a Micro-Array at Constant Temperature Capture Nucleotide Sequence Immobilisation The Diaglass slides (Eppendorf, Hamburg, Germany) are functionalized for the presence of aldehydes according to the method described in patent application WO02/18288. The protocol described in this patent application was followed for the grafting of aminated DNA to aldehyde derivatised glass. The aminated capture nucleotide sequences were spotted from solutions at concentrations of 3 μM. The capture nucleotide sequences were printed onto microscopic glass slides with a home made robotic device using 250 μm pins. The spots have 400 μm in diameter and the volume dispensed is about 0.5 nl. Slides were dried at room temperature and stored at 4° C. until used.

The capture probes are designed to be specific of DNA binding site of transcriptional factors and have the following sequences:

```
                                         (SEQ ID NO: 1)
TELK1:
5'Amine-GATGTCCTAATATGGACATCCTGTGT-3'

(SEQ ID NO: 2)
TAP1:
5'Amine-CGCTTGATGAGTCAGCCGGAACGG-3'

(SEQ ID NO: 3)
TSTAT2:
5'Amine-GATTTCTGGGAAACTGAAACTACC-3'

(SEQ ID NO: 4)
TNFAT:
5'Amine-TATGAAACAAATTTTCCTCTTTGGGCG-3'

(SEQ ID NO: 5)
TMYC:
5'Amine-TCGGAGGCCACGTGGGCGCTG-3'

(SEQ ID NO: 6)
TCREB:
5'Amine-CTAGCTCTCTGACGTCAGGCAAT-3'
```

Hybridization

The labeled probes are designed to be complementary of the immobilized capture probes and have the following sequences:

```
                                         (SEQ ID NO: 7)
PELK1:
5'-cy3-ACACAGGATGTCCATATTAGGACATC-3'

(SEQ ID NO: 8)
PAP1:
5'-cy3-CCGTTCCGGCTGACTCATCAAGCG-3'

(SEQ ID NO: 9)
PSTAT2:
5'-cy3 -GGTAGTTTCAGTTTCCCAGAAATC-3'

(SEQ ID NO: 10)
PNFAT:
5'-cy3-CGCCCAAAGAGGAAAATTTGTTTCATA-3'

(SEQ ID NO: 11)
PMYC:
5'-cy3-CAGCGCCCACGTGGCCTCCGA-3'

(SEQ ID NO: 12)
PCREB:
5'-cy3-ATTGCCTGACGTCAGAGAGCTAG-3'
```

Figure 5:
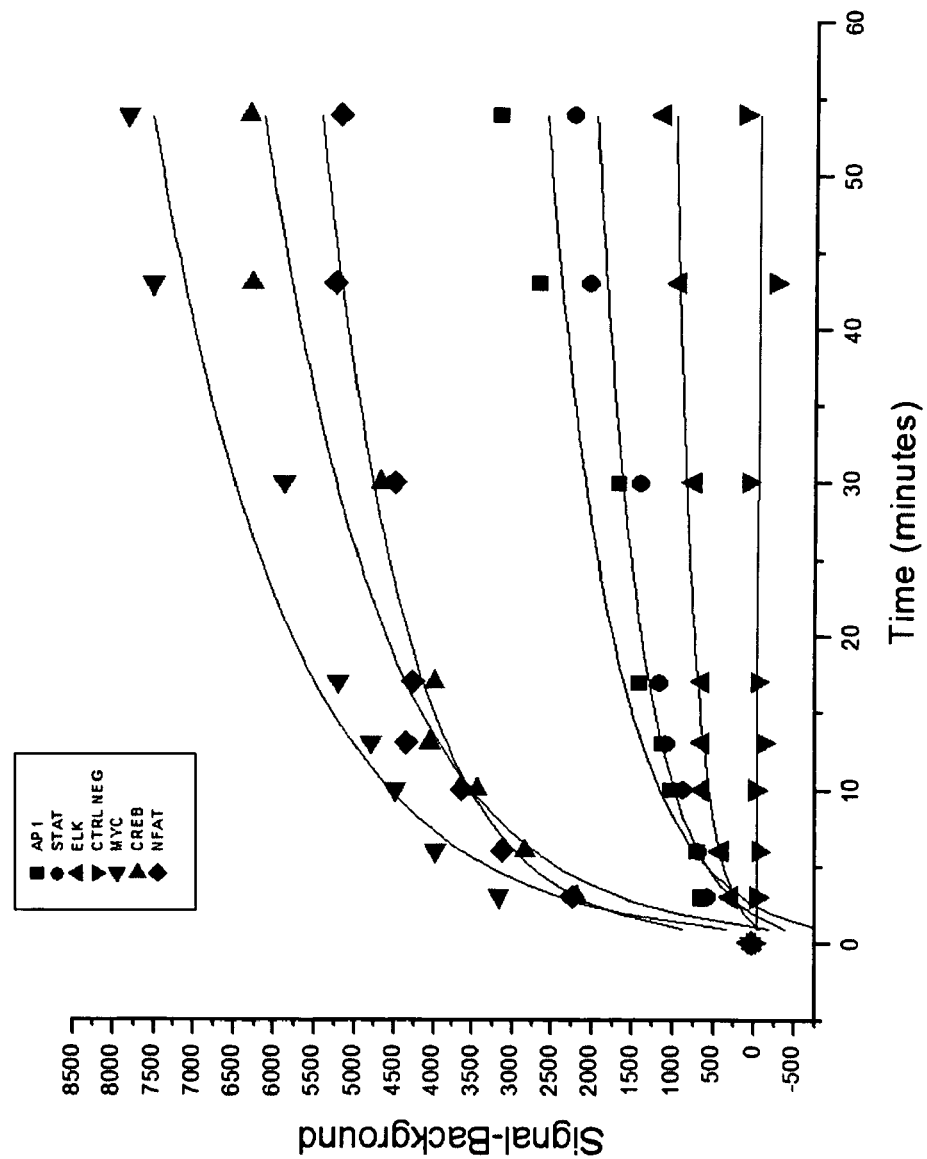
FIG. 5: Online hybridization of six different polynucleotides labeled with cy3 (PELK1, PAP1, PSTAT2, PNFAT, PMYC and PCREB) on their complementary capture molecules on micro-array. Polynucleotides are loaded on the micro-array at a concentration of 0.3 nM and are incubated at a constant temperature. A negative control (CTL−), non-specific of the capture molecules of the micro-array is simultaneously incubated.

Six polynucleotides probes labeled with Cy3 at 5' end (PELK1, PAP1, PSTAT2, PNFAT, PMYC and PCREB) have been hybridized at a concentration of 0.3 nM each in 0.2 M phosphate buffer pH 7.4 in a total volume of 25 μl on complementary capture molecules (TELK1, TAP1, TSTAT2, TNFAT, TMYC and TCREB) of a micro-array. A negative control (CTL−), non-specific of the capture molecules of the micro-array is simultaneously incubated. The solution (25 microliter) was loaded on the micro-array framed by an hybridisation chamber, of 9×9 mm and a thickness of 310 micrometers sealed with a flat coverslip and incubated at 55° C. without agitation in the thermostatized part of the apparatus which comprises a temperature control system with a precision of 1° C. The thickness of the liquid above the micro-array was 310 micrometers. Every 3 min, the slide was transferred from the incubation part of the apparatus to the scanning part, put upside down in a scanner and scanned at excitation wavelength 532. At the end of the scanning, the slide was put again in the thermostatized apparatus until the next scan. The slide was scanned at time 0, 3, 6, 9, 12, 15, 30, 45 and 55 min. In this example, the incubation part of the apparatus is physically separated from the scanning part. Results of the real-time detection are presented in FIG. 5.

Example 2

Figure 6:
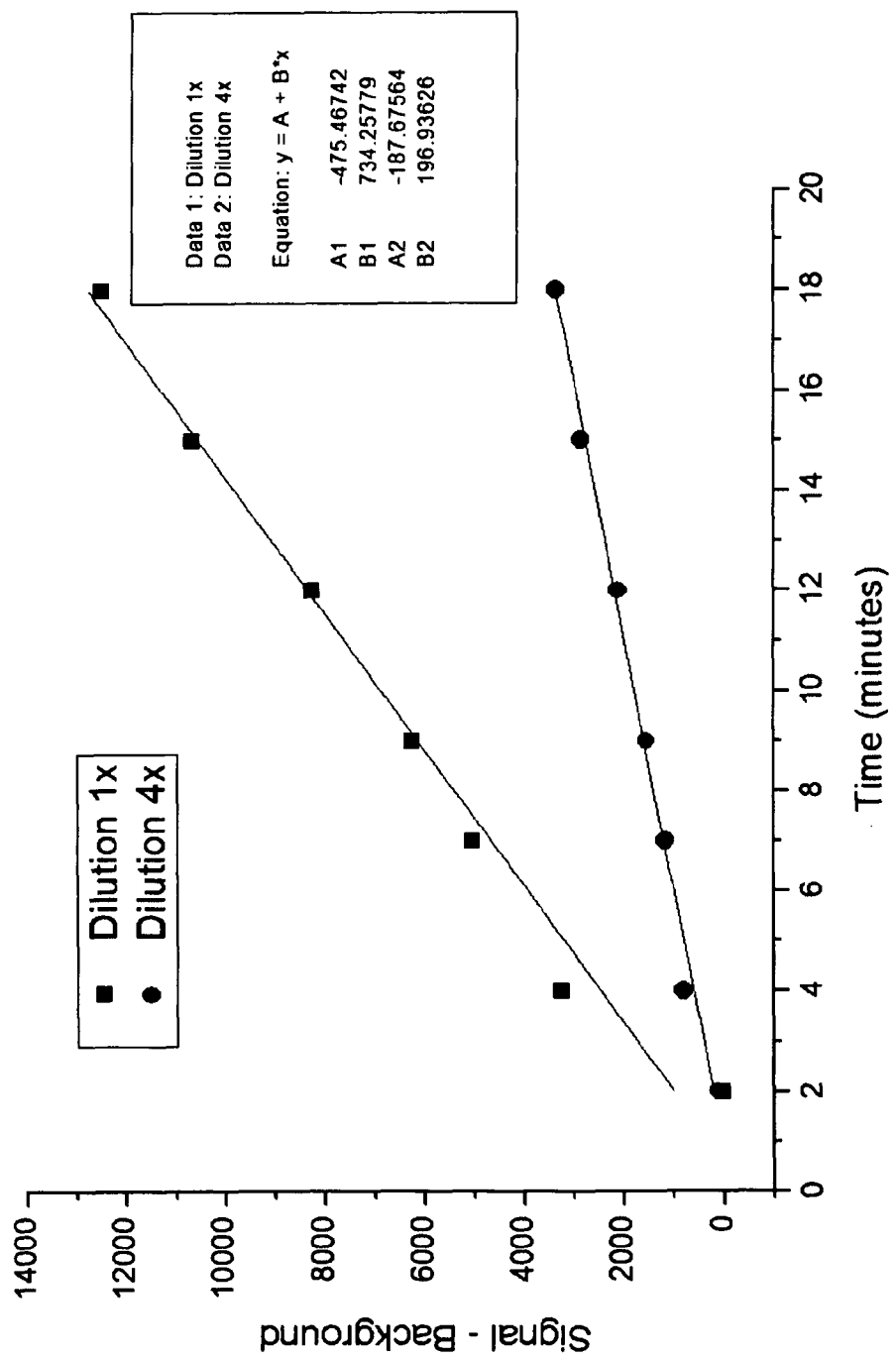
FIG. 6: Online hybridization of one polynucleotide labeled with cy3 (PAP1) at two different concentrations (1× and 4×) on complementary capture molecule of a micro-array. Each concentration of polynucleotide is incubated on a separate micro-array at 55° C.

Real-Time Hybridization of the Same Polynucleotide (CREB) at Different Concentrations on Complementary Capture Molecule of a Micro-Array at Constant Temperature The capture probe immobilization was conducted as described in example 1. One polynucleotide probe labeled with Cy3 at 5' end PAP1 (SEQ ID NO: 8) has been hybridized at three different concentrations (0.8 and 0.2 nM) in 0.2 M phosphate buffer pH 7.4 in a total volume of 25 μl on three separate micro-arrays comprising complementary capture molecule TAP1 (SEQ ID NO: 2). The solution was loaded on the micro-array and the detection was performed as explained in example 1. The slide was incubated at 55° C. and scanned at time 2, 4, 7, 9, 12, 15 and 18 min. Results of the real-time detection are presented in FIG. 6.

Example 3

Online Deshybridization of Wild Type Polynucleotides (AP1) on Complementary Capture Molecule of the Wild Type of a Micro-Array at Increasing Temperature The capture probe immobilization was conducted as described in example 1. One polynucleotide probe labeled with Cy3 at 5' end PAP1 (SEQ ID NO: 8) have been simultaneously hybridized on two capture molecules of a micro-array, one being a perfect match (TAP1 (SEQ ID NO: 2)) and one mutated (TAP1M (SEQ ID NO: 13)).

```
                                                (SEQ ID NO: 13)
TAP1M:
     5'Amine-CGCTTGATTGCTTGGCCGGAACGG-3'
```

The mutated bases as compared to the wild type TAP1 sequence are underlined.

Figure 7:
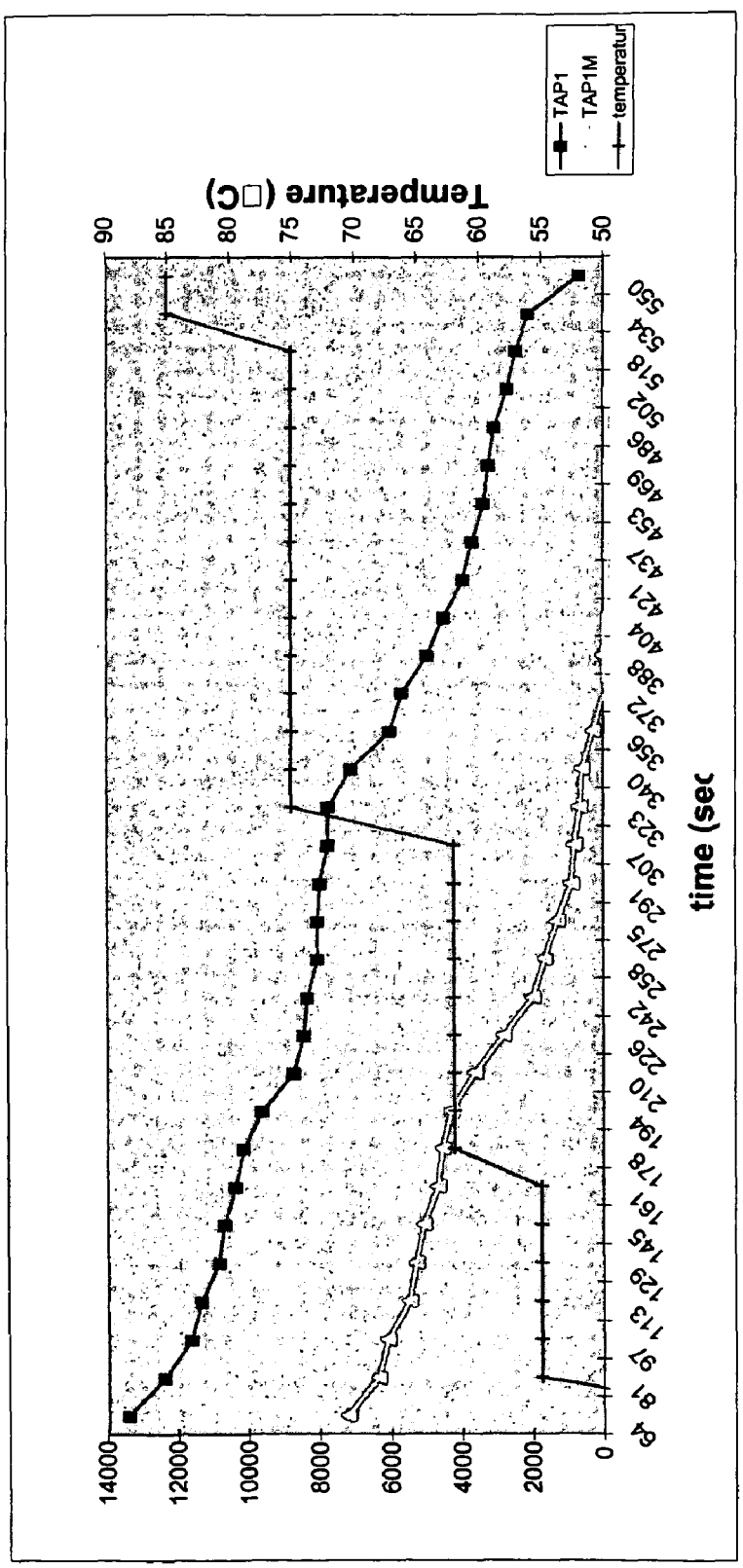
FIG. 7: Online deshybridization of wild type (PAP1) polynucleotide labeled with cy3 from the micro-array while increasing the temperature from 23 to 85° C. Two types of capture molecules are present on the micro-array: perfect match of the wild type polynucleotide (TAP1) and mutated polynucleotide (TAP1M).

The labeled polynucleotide was incubated at a concentration of 0.3 nM in 0.2 M phosphate buffer pH 7.4 in a total volume of 25 μl. The solution was loaded on the micro-array framed by an hybridisation chamber, sealed with a coverslip. The thickness of the liquid above the micro-array was 310 micrometers. The slide was incubated at 55° C. by sealing a peltier element on its back and the slide carrying the peltier is placed upside down in the scanner during the whole experiment. After 60 min at 55° C., the temperature of the peltier was decreased down to 23° C. and then increased up to 55° C. for 3 min. The temperature was then increased up to 62° C. for 4 min, then up to 75° C. for 6 min and up to 85° C. for 1 min. The micro-array was scanned every 32 sec during the incubation in the same apparatus incorporating a scanner with an excitation wavelength 532. Results are presented in FIG. 7.

Example 4

Online Detection of SNP on Micro-Array

The capture probe immobilization was conducted as described in example 1.

The capture probes used in this experiment have the following sequences:

```
                                                (SEQ ID NO: 14)
TA:      5'Amine-GCTAACTGAGCACAGGAT-3'

(SEQ ID NO: 15)
TA':     5'Amine-TAACTGAGCACGGAT-3'

(SEQ ID NO: 16)
TB:      5'Amine-GCAGTGGGTGACCGAG-3'

(SEQ ID NO: 17)
TB':     5'Amine-GCAGGGGTGACCGAGGA-3'

(SEQ ID NO: 18)
TC:      5'Amine-CCCAGGACGCCCCTTTC-3'

(SEQ ID NO: 19)
TC':     5'Amine-CCCAAGACGCCCCTTTC-3'
```

Nucleotide differences between the capture probes A, B, C and their counterpart A', B', C' are underlined. In TA' probe, there is a deletion of adenine (A) at position 5 from 3' end as compared to TA probe. In TB', deletion of thymine (T) at position 5 from the 5' end as compared to TB probe. In TC', there is a substitution (G->A) in position 5 from the 5' end.

Each capture probe comprises a spacer at its 5' end as proposed in patent application WO0177372.

Hybridization

The labeled probes are designed to be complementary of the immobilized capture probes A, B, C and have the following sequences:

```
                                                (SEQ ID NO: 20)
PA:      5'-cy3-ATCCTGTGCTCAGTTAGC-3'

(SEQ ID NO: 21)
PB:      5'-cy3-CTCGGTCACCCACTGC-3'

(SEQ ID NO: 22)
PC:      5'-cy3-GAAAGGGGCGTCCTGGG-3'
```

Three polynucleotides probes (PA (SEQ ID NO: 20), PB (SEQ ID NO: 21), PC (SEQ ID NO: 22) labeled with Cy3 at 5' end, which are specific respectively of capture molecules A, B and C (TA (SEQ ID NO: 14), TB (SEQ ID NO: 16, TC (SEQ ID NO: 18), have been hybridized at a concentration of 0.3 nM in 0.2 M phosphate buffer pH 7.4 in a total volume of 25 μl on the same micro-array comprising also mutated capture molecule (TA' (SEQ ID NO: 15), TB' (SEQ ID NO: 17), TC' (SEQ ID NO: 19).

Figure 8:
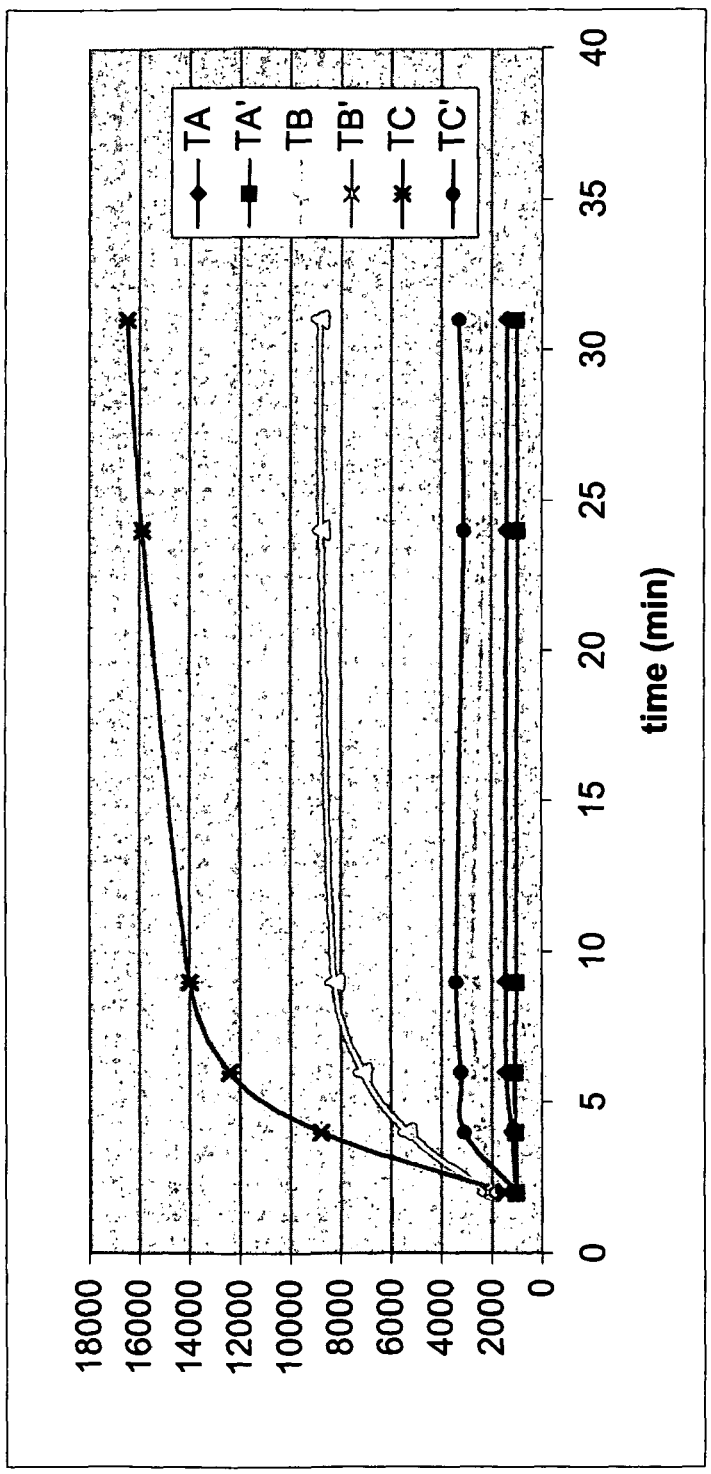
FIG. 8: Online detection of SNP on micro-array. Effect of the probe sequence on the specificity of hybridization. Three polynucleotides cy3 labeled (PA, PB, PC) are hybridized on their complementary capture molecules (TA, TB, TC) on micro-array in the presence of mutated capture molecules (TA', TB', TC') at 65° C.

The solution was loaded on the micro-array and processed as in example 3. Specific (on TA, TB, TC capture probes) and non-specific hybridization (on TA', TB', TC' capture probes) have been followed with time by scanning the micro-array at time 2, 4, 6, 9, 24 and 31 min. Result of the online detection at 65° C. is presented in FIG. 8. This result shows the effect of the probe on the specificity of hybridization: probe PC is the most discriminating, PB is also discriminating but less than PC and PA is non discriminating.

Temperature (50° C. and 65° C.) has a clear effect on SNP detection. At 65° C., there is a good discrimination for probe PC while no discrimination was observed at 50° C.

Example 5

Online Detection of Antibody Binding on their Respective Antigen on a Micro-Array Capture Protein Immobilisation The Diaglass slides (Eppendorf, Hamburg, Germany) are functionalized for the presence of aldehydes according to the method described in patent application WO02/18288. The protocol described in this patent application was followed for the grafting of antibodies to aldehyde derivatised glass. The antibodies were spotted from solutions at concentrations of 200 μM. The capture nucleotide sequences were printed onto microscopic glass slides with a home made robotic device using 250 μm pins. The spots have 400 μm in diameter and the volume dispensed is about 0.5 nl. Slides were dried at room temperature and stored at 4° C. until used.

The antibodies were purchased from different providers as follows:

Mouse antibodies: A (Santa Cruz, No. SC-7972), B (Upstate, No. 05-454), C (BD, No. 612.169), D (Biosource, No. AH00782), E (R&D, No. MAB869), F (Cell signaling, No. 9216), G (Santa Cruz, No. SC-7973), H (BD, No. 612.281), I (BD, No. 612.289).

Rabbit antibodies: A' (Sigma, No. M0800), B' (Santa Cruz, No. SC-535), C' (Santa Cruz, No. SC-728), D' (Santa Cruz, No. SC-7149), E' (R&D, No. AF8691), F' (R&D, No. AF869), G' (Biosource, No. 44 684 Z), H' (Santa Cruz, No. SC-7975-R).

Antibodies Reaction on the Micro-Array

Figure 9:
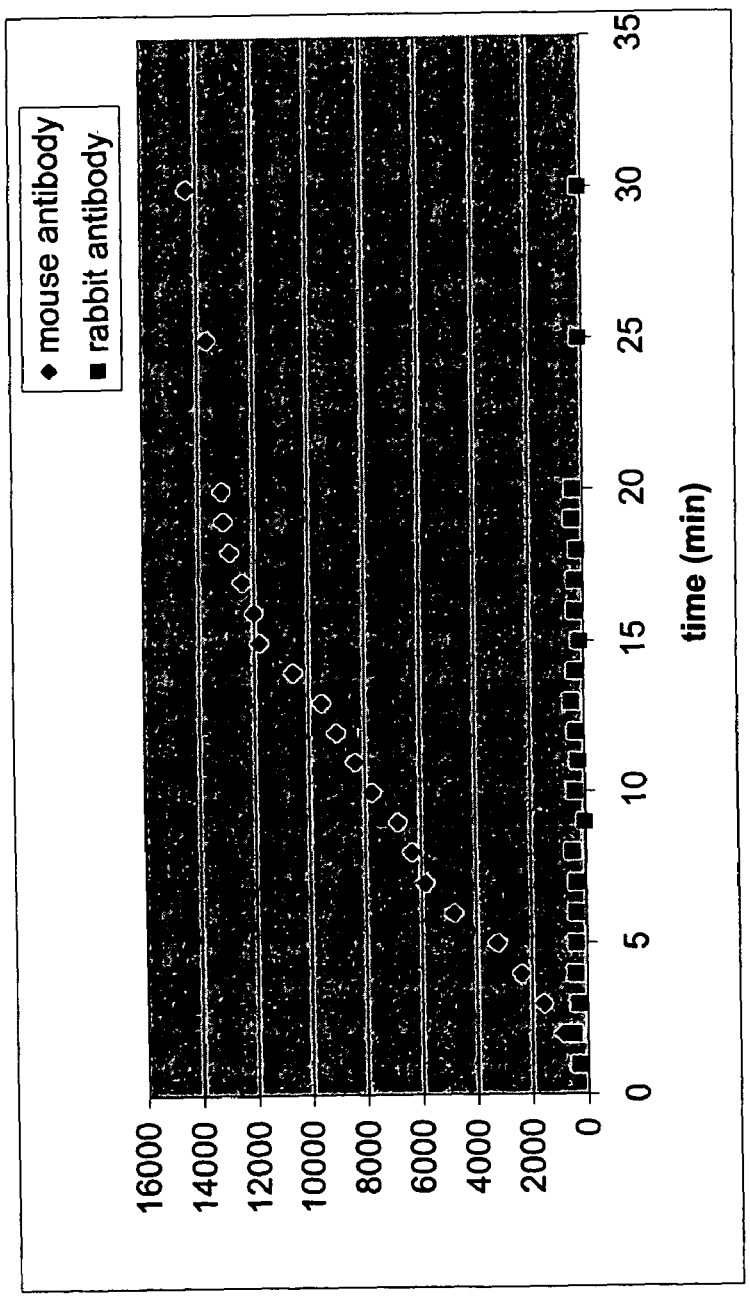
FIG. 9: Online detection of antibodies. A goat anti-mouse antibody cy3 labeled is detected in real-time for its binding on a mouse antibody on a micro-array in the presence of immobilized rabbit antibody. Detection Images are taken during 30 min incubation.

A micro-array have been spotted with 9 different mouse antibodies (A-I) and 8 different rabbit antibodies (A'-H') at 2 concentrations (200 μg/ml and 20 μg/ml). Solutions were loaded on the micro-array and the detection was performed as explained in example 3. Goat anti-rabbit antibody labeled with Cy3 (Jackson Immunoresearch, No. 111-165-003) diluted 1000× in PBS+BSA 1%+Tween 0.5% was incubated on the micro-array for 30 min in a chamber in a final volume of 25 μl. On a second array, goat anti-mouse antibody labeled with Cy3 (Jackson Immunoresearch, No. 115-165-003) diluted 1000× was processed similarly. The incubation is made at 20° C. inside the same apparatus incorporating a scanner with the slide upside down. Specific and non-specific reactions have been followed online by scanning the micro-array every min until 20 min and then every 5 min until 30 min incubation. Results on FIG. 9 shows the online detection of a mouse antibody spotted at 200 µg/ml (I, BD, No. 612.289). and a rabbit antibody spotted at 200 µg/ml (A', Sigma, No. M0800) with a goat anti-mouse antibody-Cy3 during 30 min.

Example 6

Real-Time Detection of cDNA on Micro-Array cDNA Synthesis

1 µl of total RNA (10 µg/µl) from rat liver (Ambion) was mixed with 2 µl oligo(dT)12-18 (0.5 µg/µl, Roche), 3.5 µl H2O, and 2 µl of a solution of 6 different synthetic well-defined poly(A+) RNAs. These latter served as internal standards to assist in quantification and estimation of experimental variation introduced during the subsequent steps of analysis. The 6 Internal standard RNA are present at different concentrations: IS1=10 ng/ml, IS2=1 ng/ml, IS3=100 pg/ml, IS4=30 pg/ml, IS5=10 pg/ml, IS6=5 pg/ml.

After an incubation of 10 min at 70° C. and 5 minutes on ice, 9 µl of reaction mix were added. Reaction mix consisted in 4 µl Reverse Transcription Buffer 5× (Gibco BRL), 1 µl RNAsin Ribonuclease Inhibitor (40 U/ml, Promega), and 2 µl of a 10× dNTP mix, made of dATP, dTTP, dGTP (5 mM each, Roche), dCTP (800 µM, Roche), and Cy3-dCTP (800 µM, NEN).

After 5 minutes at room temperature, 1.5 µl SuperScript 11 (200 U/ml, Gibco BRL) was added and incubation was performed at 42° C. for 90 minutes. Addition of SuperScript and incubation were repeated once. The mixture was then placed at 70° C. for 15 minutes and 1 µl Ribonuclease H (2 U/µl) was added for 20 minutes at 37° C. Finally, a 3-minutes denaturation step was performed at 95° C. After reverse transcription step, the RT product is purified from free dCTP-Cy3 on a G25 spin column (Pierce, #89849). The purified fluorescent cDNA, was kept at −20° C.

Hybridization with Cy3 cDNA

Figure 10:
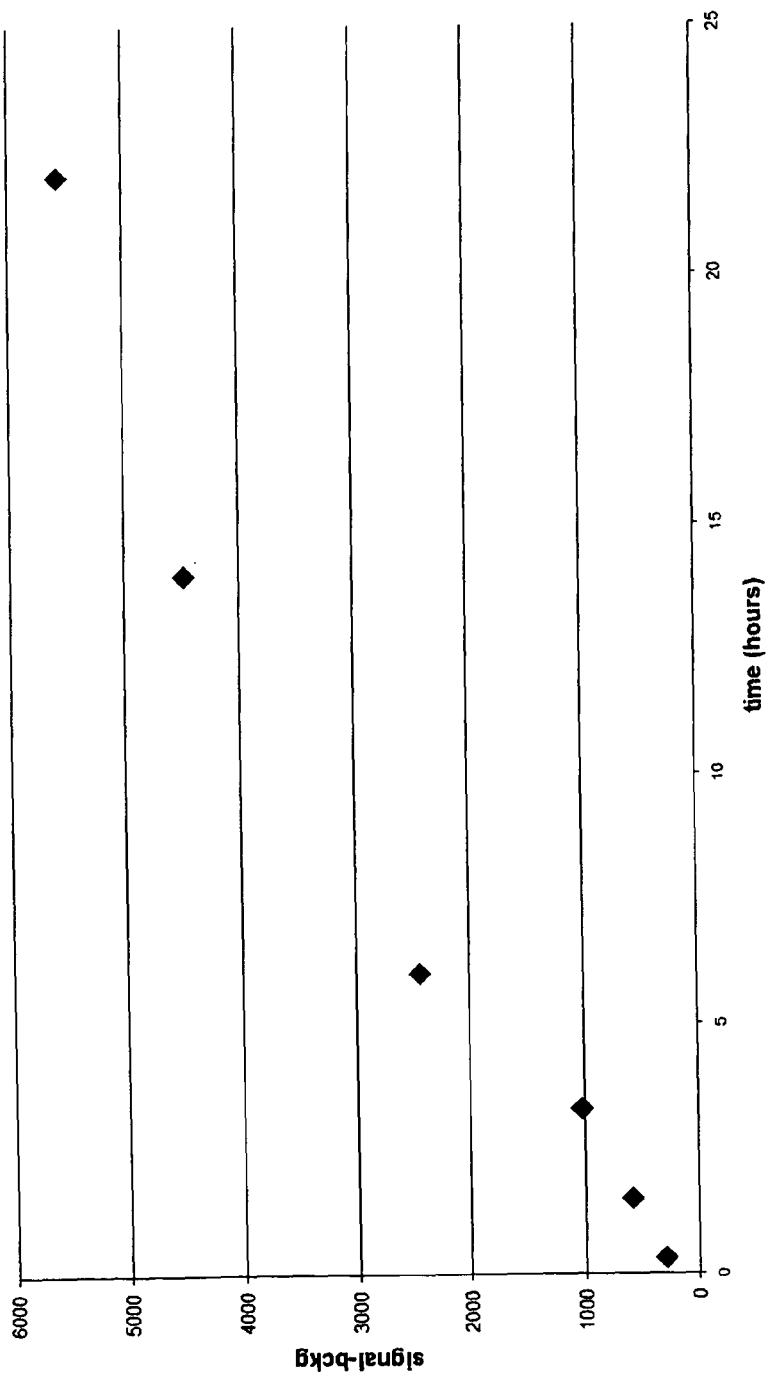
FIG. 10: Online hybridization of cy3 labeled single stranded cDNA (IS1) on complementary capture molecule of a micro-array. Detection Images are taken during 22 hours incubation.
Figure 11:
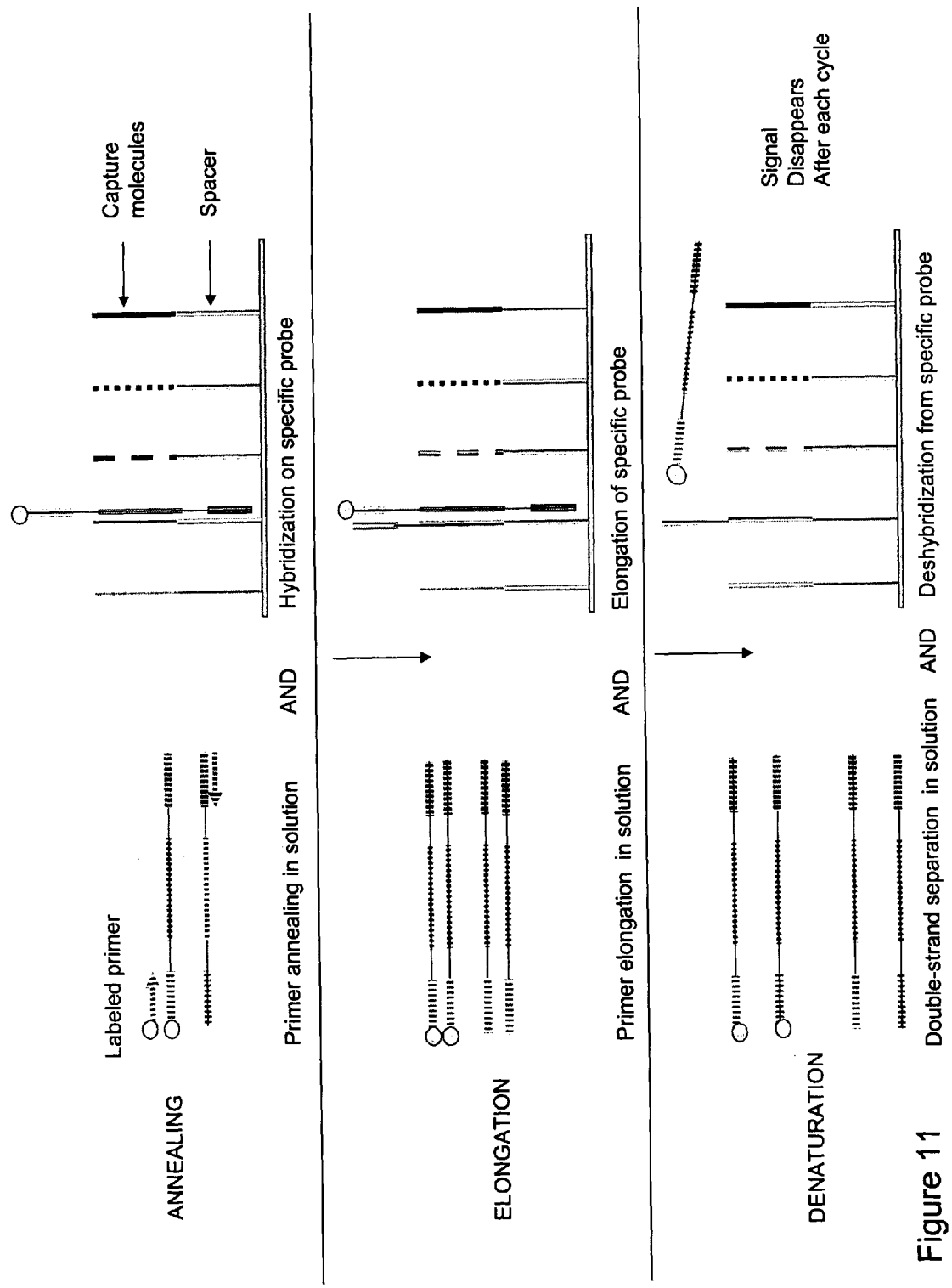
FIG. 11: Online detection of PCR product on micro-array using labeled primer. PCR is performed in the presence of a micro-array comprising different capture molecules. Alternate steps of annealing, elongation and denaturation during one cycle of reaction result in the accumulation of labeled products which hybridize on their capture molecule present on the micro-array but deshybrizes from their specific capture molecules after each denaturation cycle.
Figure 12:
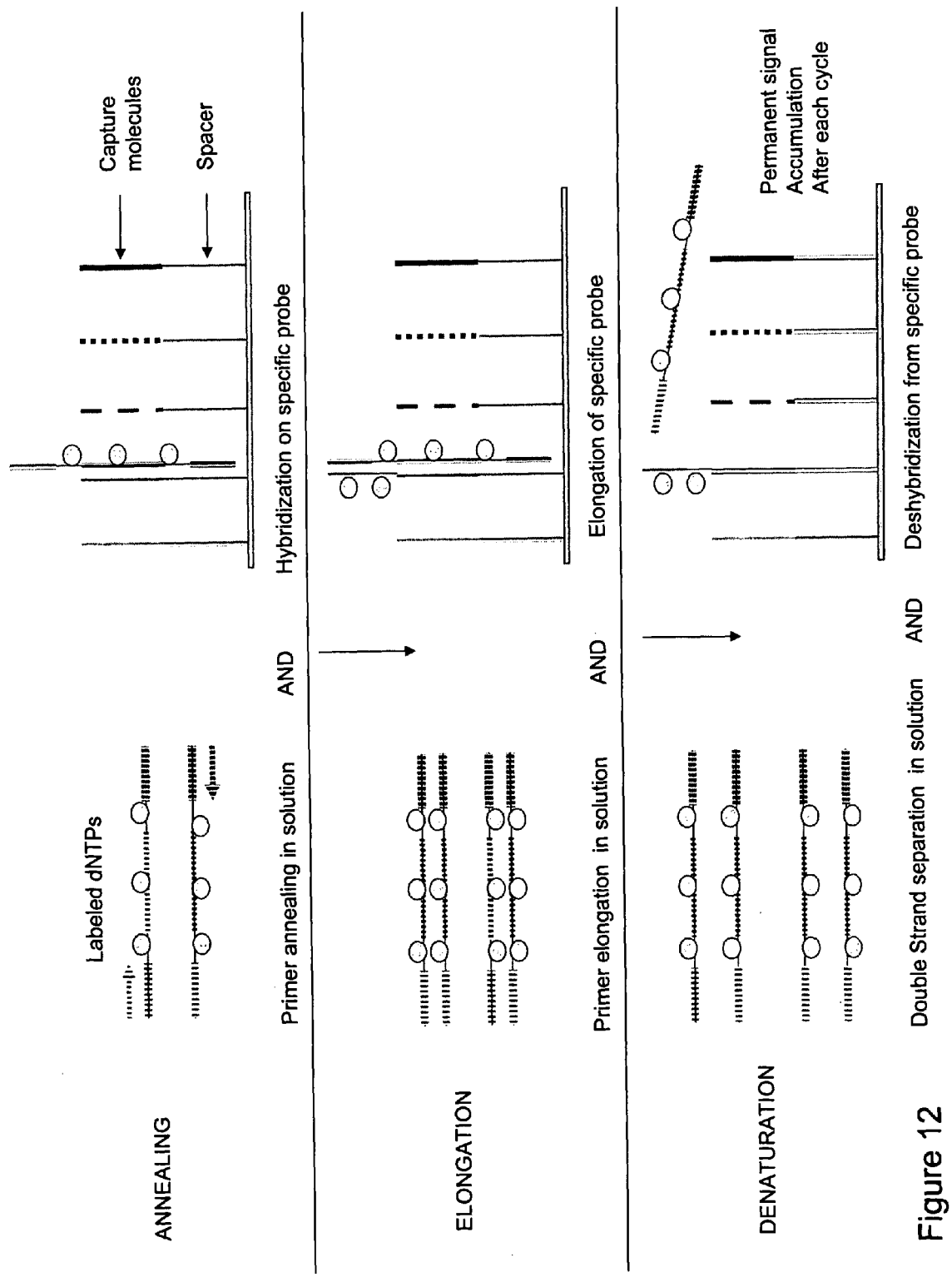
FIG. 12: Online detection of PCR product on micro-array using labeled dNTPs. PCR is performed in the presence of a micro-array comprising different capture molecules. Alternate steps of annealing, elongation and denaturation during one cycle of reaction result in the accumulation of labeled product which is partly integrated into its specific capture molecule after each denaturation cycle and detected.

20 µl of purified and Cy3 labeled RT product was hybridized onto a DualChip rat hepato (Eppendorf, Hamburg, Germany) in SSC 2×SDS 4% in a total volume of 25 µl. The solution was loaded on the micro-array and the detection was performed as explained in example 1. The slide was incubated for 22 hours at 65° C. mixing at 1400 rpm in the incubation part of the apparatus. At the time of reading, the agitation was stopped and the slide was transferred to the scanning part of the apparatus, put upside down and scanned at excitation wavelength 532., The slide was scanned at time 2 min, 90 min, 200 min, 6 hours, 14 hours and 22 hours. FIG. 10 presents the real-time hybridization of IS1 cDNA.

We claim:

1. A method for real-time quantification of multiple target molecules on a micro-array comprising the steps of:
    placing, in a reaction chamber, a support having fixed upon its surface a micro-array comprising at least 5 capture molecules each being immobilized in specifically localized areas of said support,
    introducing a solution containing labeled target molecules into the reaction chamber such that the thickness of the solution in contact with the micro-array is constant above all the localized areas,
    incubating said labeled target molecules under conditions allowing a specific binding between said targets and their corresponding capture molecules,
    directing and focusing an excitation light from a light source onto the surface of the support such that the light reaches the micro-array surface at an angle comprised between 45° and 135°, wherein the excitation is directed and focused on the support through the solution and wherein the difference of thickness of the solution above the localized areas is less than 100 µm, less than 10 µm or less than 1 µm,
    measuring the light emission from bound target molecules in response to said excitation light in the presence of the solution containing the labeled target molecules, wherein the surface of emission for a localized area is comprised between about 0.1 µm$^2$ and about 10 mm$^2$ and wherein each of at least 4 localized areas is monitored with time with at least two measurements being done per localized area, and
    processing and storing the values of the different measurements and quantifying at least 4 different target molecules present in the solution using at least one measurement value for each said target.

2. The method of claim 1, wherein the target molecules are labeled with a fluorescent dye.

3. The method of claim 2, wherein the fluorescent dye is cyanin 3.

4. The method of claim 1, wherein the target molecules are nucleic acids.

5. The method of claim 1, wherein the target molecules are homologous nucleotide sequences.

6. The method of claim 1, wherein the target molecules are proteins.

7. The method of claim 6, wherein the proteins are selected from the group consisting of antibody, antigen, ligand, and receptor.

8. The method of claim 1, wherein the temperature during the binding reaction is controlled and stable with a variation of less than 5° C. or less than 1° C.

9. The method of claim 1, wherein the measurement is performed between 1 min and 24 h.

10. The method of claim 9, wherein the temperature is held constant for at least 1 min during the calculation period.

11. The method of claim 9, wherein the temperature is held constant for between 1 and 5 min during the calculation period.

12. The method of claim 9, wherein the temperature is stable for between 1 and 60 min during the calculation period.

13. The method of claim 9, wherein the temperature is stable for between 1 min and 24 h during the calculation period.

14. The method of claim 1, wherein the concentration of the target molecules is comprised between about 0.0001 and about 1000 nM in the detection solution.

15. The method of claim 1, wherein the concentration of the target molecules is comprised between about 0.001 and about 10 nM in the detection solution.

16. The method of claim 1, wherein the support bearing the capture molecules is glass.

17. The method of claim 1, wherein the support contains a substrate on which are fixed the capture molecules.

18. The method of claim 1, wherein the micro-array contains more than 20 different capture molecules and less than 1000.

19. The method of claim 1, wherein the capture molecules are deposited by physical means on the substrate.

20. The method of claim 1, wherein the capture molecules are synthesized in situ on the substrate in predefined locations.

21. The method of claim 1, wherein the capture molecules are present in defined locations on the substrate.

22. The method of claim 1, wherein the surface of emission of the localized area for the detection of a target is comprised between 1 $\mu m^2$ and 1 $mm^2$.

23. The method of claim 1, wherein the surface of the support bearing the capture molecules has a 3 dimensional structure.

24. The method of claim 1, wherein the support bears several micro-arrays separated by physical boundaries.

25. The method of claim 24, wherein the support has a multi-well format.

26. The method of claim 1, wherein the calculation of the concentration of a target present in solution is derived from the calculation of the kinetic coefficient of the signal appearance with time in the localized area to which the target binds in a specific manner.

27. The method of claim 1, wherein the calculation of the concentration of the target present in solution is derived from the first order kinetic coefficient of the signal taken from at least 3 values taken with time in the localized area to which the target binds specifically.

28. The method of claim 1, wherein the solution containing the target molecules is submitted to temperature cycles having at least 2 and preferably 3 different temperatures between two or more measurements.

29. The method of claim 28, wherein the temperature cycles and the reaction conditions are those which produce a PCR.

* * * * *